(12) United States Patent
Blaschuk et al.

(10) Patent No.: US 6,680,175 B2
(45) Date of Patent: Jan. 20, 2004

(54) METHODS FOR DIAGNOSING AND EVALUATING CANCER

(75) Inventors: Orest W. Blaschuk, Westmount (CA); James Matthew Symonds, Ottawa (CA); Stephen Byers, Washington, DC (US); Barbara J. Gour, Montreal (CA)

(73) Assignee: Adherex Technologies, Inc., Ottawa (CA)

( * ) Notice: Subject to any disclaimer, the term of this patent is extended or adjusted under 35 U.S.C. 154(b) by 0 days.

(21) Appl. No.: 09/234,395

(22) Filed: Jan. 20, 1999

(65) Prior Publication Data

US 2002/0123044 A1 Sep. 5, 2002

Related U.S. Application Data

(63) Continuation-in-part of application No. 09/187,859, filed on Nov. 6, 1998, now Pat. No. 6,358,920, which is a continuation-in-part of application No. 09/073,040, filed on May 5, 1998, now Pat. No. 6,472,367.

(51) Int. Cl.$^7$ .................. G01N 33/574; G01N 33/567; G01N 33/53

(52) U.S. Cl. ............... 435/7.23; 435/7.1; 435/7.21; 435/7.2

(58) Field of Search ............... 424/138.1, 130.1, 424/143.1, 156.1; 435/71, 7.23

(56) References Cited

U.S. PATENT DOCUMENTS

| | | | |
|---|---|---|---|
| 5,597,725 A | 1/1997 | Suzuki | |
| 5,639,634 A | 6/1997 | Suzuki | |
| 5,646,250 A | 7/1997 | Suzuki | |
| 5,811,514 A | 9/1998 | Bard et al. | |
| 5,895,748 A | * 4/1999 | Johnson et al. | |
| 5,916,771 A | 6/1999 | Hori et al. | |
| 5,997,866 A | * 12/1999 | Johnson et al. | |
| 6,031,072 A | 2/2000 | Blaschuk et al. | 530/317 |

FOREIGN PATENT DOCUMENTS

| | | |
|---|---|---|
| GB | 2 282 379 A | 4/1995 |
| WO | WO 91/04745 | 4/1991 |
| WO | WO 96/27387 | 9/1996 |
| WO | WO 98/02452 | 1/1998 |
| WO | WO 00/02917 | 1/2000 |

OTHER PUBLICATIONS

Munro, S. et al. Experimental and Molecular Pathology, 62(2): 118–122, 1995 abstract only.*

Wheelock, M. et al. Journal of Cellular Biochemistry, 34: 187–202, 1987 pp. 187–190 only.*

Taber's Cyclopedia Medical Dictionary 17th edition(1993) p. 1016.*

The Merck Manual of Diagnosis and Therapy 16th edition (1992) p. 1265.*

Vallin et al., Mechanisms of Development (1998) abstract.*

Bangma et al., "The Value of Screening Tests in the Detection of Prostate Cancer. Part I: Results of a Retrospective Evaluation of 1726 Men," *Urology* 46(6):773–778, 1995.

Griffiths et al., "Cell adhesion molecules in bladder cancer: soluble serum E–cadherin correlates with predictors of recurrence," *Br. J. Cancer* 74: 579–584, 1996.

Katayama et al., "Soluble E–cadherin fragments increased in circulation of cancer patients," *Br. J. Cancer 69:* 580–585, 1994.

Loric et al., "Enhanced Detection of Hematogenous Circulating Prostatic Cells in Patients with Prostate Adenocarcinoma by Using Nested Reverse Transcription Polymerase Chain Reaction Assay Based on Prostate–Specific Membrane Antigen," *Clin. Chem.* 41(12): 1698–1704, 1995.

Matsuoka et al., "Recognition of Ovarian Cancer Antigen CA125 by Murine Monoclonal Antibody Produced by Immunization of Lung Cancer Cells," *Cancer Res. 47:* 6335–6340, Dec. 1, 1987.

Mulders et al., "Prostate–specific antigen (PSA). A tissue–specific and sensitive tumor marker," *Eur. J . Surg. Oncol. 16:* 37–41, 1990.

Rustin et al., "Defining Response of Ovarian Carcinoma to Initial Chemotherapy According to Serum CA 125," *J. Clin. Oncol.* 14(5): 1545–1551, May 1996.

Tsutsui et al., "Expression of Cadherin–Catenin Complexes in Human Leukemia Cell Lines," *J. Biochem. 120:* 1034–1039, 1996.

Van Den Brüle et al., "Genes Involved in Tumor Invasion and Metastasis are Differentially Modulated by Estradiol and Progestin in Human Breast–Cancer Cells," *Int. J. Cancer 52:* 653–657, 1992.

Kimura, Y. et al., "Cadherin–11 Expressed in Association with Mesenchymal Morphogenesis in the Head, Somite, and Limb Bud of Early Mouse Embryos," *Developmental Biology 169:* 347–358, 1995.

Kools, P.F.J. et al., "Expression in mesenchymal tumors of alternative cadherin–11 transcripts encoding truncated adhesion molecules: a mechanism for acquiring invasive properties?" *Clinical & Experimental Metastasis* 14(Suppl. 1): 52–53, Sep. 1996.

(List continued on next page.)

Primary Examiner—Marianne P. Allen
(74) Attorney, Agent, or Firm—Seed Intellectual Property Law Group PLLC

(57) ABSTRACT

Methods for diagnosing cancer, such as prostate, ovarian or breast cancer, as well as leukemia, are provided. Such methods may employ binding agents, such as antibodies or CAR sequences of OB-cadherin or N-cadherin, that specifically bind to OB-cadherin or N-cadherin, or polynucleotides that hybridize to a polynucleotide encoding OB-cadherin or N-cadherin. Also provided are methods for monitoring the progression of a cancer and to evaluate the metastatic potential of a cancer.

6 Claims, 4 Drawing Sheets

OTHER PUBLICATIONS

Pishvaian, M.J. et al., "Cadherin–11 Is Expressed in Invasive Breast Cancer Cell Lines," *Cancer Research 59:* 947–952, Feb. 15, 1999.

Bussemakers et al., "The role of OB–cadherin in human prostate cancer," in *Proceedings of the American Association for Cancer Research,* vol. 39, New Orleans, LA, Mar., 1998, p. 500.

Albeda et al., "Adhesion Molecules and Inflammatory Injury," *FASEB J. 8*(8): 504–512, 1994.

Edgington, "How Sweet It Is: Selectin–Mediating Drugs," *Bio/Technology 10*(4): 383–389, 1992.

Kahan, "Immunosuppressive Therapy," *Current Opinion in Immunology 4*(5): 553–560, 1992.

Lutz et al., "Antibody Recognition of Peptide Sequences from the Cell—Cell Adhesion Proteins: N– and E–cadherins," *Peptide Research 9*(5): 233–239, 1996.

Slootstra et al., "Structural Aspects of Antibody–Antigen Interaction Revealed Through Small Random Peptide Libraries," *Molecular Diversity 1:* 87–96, 1995.

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communication 2:* 15–26, 1994.

Ward and Mulligan, "Blocking of Adhesion Molecules In Vivo as Anti–Inflammatory Therapy," *Therapeutic Immunology 1:* 165–171, 1994.

Doherty and Walsh, "CAM–FGF Receptor Interactions: A Model for Axonal Growth," *Molecular and Cellular Neuroscience 8:* 99–111, 1996.

Doherty and Walsh, "Signal transduction events underlying neurite outgrowth stimulated by cell adhesion molecules," *Current Opinion in Neurobiology 4:* 1 49–55, 1994.

Getsios et al., "Regulated Expression of Cadherin–6 and Cadherin–11 in the Glandular Epithelial and Stromal Cells of the Human Endometrium," *Developmental Dynamics 211:* 238–247, 1998.

Hall et al., "Review: A Role for the FGF Receptor in the Axonal Growth Response Stimulated by Cell Adhesion Molecules?," *Cell Adhesion and Communication 3:* 441–450, 1996.

Matsuyoshi and Imamura, "Multiple Cadherins Are Expressed in Human Fibroblasts," *Biochemical And Biophysical Research Communications 235:* 355–358, 1997.

Munro and Blaschuk, "A Comprehensive Survey of the Cadherins Expressed in the Testes of Fetal, Immature, and Adult Mice Utilizing the Polymerase Chain Reaction," *Biology of Reproduction 55:* 822–827, 1996.

Munro and Blashchuk, In: *Cell Adhesion and Invasion in Cancer Metastasis,* P. Brodt (ed.), RG Landes Co., Austin, Texas, 1996, Chapter 3, "The Structure, Function and Regulation of Cadherins," pp. 17–34.

Okazaki et al., "Molecular Cloning and Characterization of OB–cadherin, a New Member of Cadherin Family Expressed in Osteoblasts," *The Journal of Biological Chemistry 269*(16): 12092–12098, 1994.

Saffell et al., "Expression of a Dominant Negative FGF Receptor Inhibits Axonal Growth and FGF Receptor Phosphorylation Stimulated by CAMs," *Neuron 18:* 231–242, 1997.

Shibata et al., "Simultaneous expression of cadherin–11 in signet–ring cell carcinoma and stromal cells of diffuse–type gastric cancer," *Cancer Letters 99:* 147–153, 1996.

Shimazui et al., "Complex Cadherin Expression in Renal Cell Carcinoma," *Cancer Research 56:* 3234–3237, 1996.

Simonneau et al., "Cadherin 11 Expression Marks the Mesenchymal Phenotype: Towards New Functions for Cadherins?," *Cell Adhesion and Communication 3:* 115–130, 1995.

Suzuki et al., "Diversity of the cadherin family: evidence for eight new cadherins in nervous tissue," *Cell Regulation 2:* 261–270, 1991.

Williams et al., "Activation of the FGF Receptor Underlies Neurite Outgrowth Stimulated by L1, N–CAM, and N–Cadherin," *Neuron 13:* 583–594, 1994.

are 74:

\* cited by examiner

Human G W V W N Q F F V I N M V T G P D P V L V G R L H S D I D S G D G N I K Y I L S G E G A G
Mouse G W V W N Q F F V I N M V I G P D P V L V G R L H S D I D S G D G N I K Y I L S G E G A G Human T I F V I D M N B G N I H A T K T L D R E E R A Q Y T L M A Q A V D R D T N R P L E P P S
Mouse T I F V I D M N B G N I H A T K T L D R E E R A Q Y T L M A Q A V D R D T N R P L E P P S Human N F I V K V Q D I N D N P P E F
Mouse N F I V K V Q D I N D N P P E F

*Fig. 2* human N cad DWVIPPINNPENSRGPFPQELVRIRSDRDKNLSLRYSVTGPGADQPPTGIFILNPISGQLSVTKPLDREQ
mouse N cad DWVIPPINNPENSRGPFPQELVRIRSDRDKNLSLRYSVTGPGADQPPTGIFILNPISGQLSVTKPLDREL
  cow N cad DWVIPPINNPENSRGPFPQELVRIRSDRDKNLSLRYSVTGPGADQPPTGIFILNPISGQLSVTKPLDREL human N cad IARFHLRAHAVDINGNQVENPIDIVINVIDMNDNRPEF
mouse N cad IARFHLRAHAVDINGNQVENPIDIVINVIDMNDNRPEF
  cow N cad IARFHLRAHAVDINGNQVENPIDIVINVIDMNDNRPEF

*Fig. 3*

SEQUENCE LISTING

```
<160> NUMBER OF SEQ ID NOS: 324

<210> SEQ ID NO 1
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<220> FEATURE:
<223> OTHER INFORMATION: Description of Unknown Organism:  Calcium Binding
      Motif in Extracellular domains of Classical
      Cadherins

<400> SEQUENCE: 1

Asp Xaa Asn Asp Asn
1               5

<210> SEQ ID NO 2
<211> LENGTH: 4
<212> TYPE: PRT
<213> ORGANISM: Unknown
<220> FEATURE:
<223> OTHER INFORMATION: Description of Unknown Organism:  Calcium Binding
      Motif in Extracellular domains of Classical
      Cadherins

<400> SEQUENCE: 2

Leu Asp Arg Glu
1
```

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 3

Ile Phe Val Ile Asp Asp Lys Ser Gly
1               5

<210> SEQ ID NO 4
<211> LENGTH: 106
<212> TYPE: PRT
<213> ORGANISM: Homo sapiens

<400> SEQUENCE: 4

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
                20                  25                  30

Gly Asn Ile Lys Tyr Ile Leu Ser Gly Glu Gly Ala Gly Thr Ile Phe
            35                  40                  45

Val Ile Asp Asp Lys Ser Gly Asn Ile His Ala Thr Lys Thr Leu Asp
50                  55                  60

Arg Glu Glu Arg Ala Gln Tyr Thr Leu Met Ala Gln Ala Val Asp Arg
65                  70                  75                  80

Asp Thr Asn Arg Pro Leu Glu Pro Pro Ser Glu Phe Ile Val Lys Val
                85                  90                  95

Gln Asp Ile Asn Asp Asn Pro Pro Glu Phe
            100                 105

<210> SEQ ID NO 5
<211> LENGTH: 106
<212> TYPE: PRT
<213> ORGANISM: Mus musculus

<400> SEQUENCE: 5

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
                20                  25                  30

Gly Asn Ile Lys Tyr Ile Leu Ser Gly Glu Gly Ala Gly Thr Ile Phe
            35                  40                  45

Val Ile Asp Asp Lys Ser Gly Asn Ile His Ala Thr Lys Thr Leu Asp
50                  55                  60

Arg Glu Glu Arg Ala Gln Tyr Thr Leu Met Ala Gln Ala Val Asp Arg
65                  70                  75                  80

Asp Thr Asn Arg Pro Leu Glu Pro Pro Ser Glu Phe Ile Val Lys Val
                85                  90                  95

Gln Asp Ile Asn Asp Asn Pro Pro Glu Phe
            100                 105

<210> SEQ ID NO 6
<211> LENGTH: 108
<212> TYPE: PRT
<213> ORGANISM: Homo sapiens

<400> SEQUENCE: 6

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Leu Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
                100                 105

<210> SEQ ID NO 7
<211> LENGTH: 108
<212> TYPE: PRT
<213> ORGANISM: Mus musculus

<400> SEQUENCE: 7

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
    50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
                100                 105

<210> SEQ ID NO 8
<211> LENGTH: 108
<212> TYPE: PRT
<213> ORGANISM: Bos taurus

<400> SEQUENCE: 8

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
    50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
                100                 105

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (9)
<223> OTHER INFORMATION: AMIDATION

<400> SEQUENCE: 9

Ile Phe Val Ile Asp Asp Lys Ser Gly
 1               5

<210> SEQ ID NO 10
<211> LENGTH: 9
<212> TYPE: PRT
<213> ORGANISM: Unknown
<220> FEATURE:
<223> OTHER INFORMATION: Description of Unknown Organism: Consensus Cell
      Adhesion Recognition Sequence in an OB-Cadherin
<220> FEATURE:
<221> NAME/KEY: MOD_RES
<222> LOCATION: (1)
<223> OTHER INFORMATION: Where Xaa is and independently selected amino
      acid
<220> FEATURE:
<221> NAME/KEY: MOD_RES
<222> LOCATION: (3)
<223> OTHER INFORMATION: Where Xaa is either Valine of Serine
<220> FEATURE:
<221> NAME/KEY: MOD_RES
<222> LOCATION: (4)
<223> OTHER INFORMATION: Where Xaa is either Isoleucine or Valine
<220> FEATURE:
<221> NAME/KEY: MOD_RES
<222> LOCATION: (5)
<223> OTHER INFORMATION: Where Xaa is either Aspartate or Glutamate
<220> FEATURE:
<221> NAME/KEY: MOD_RES
<222> LOCATION: (6)
<223> OTHER INFORMATION: Where Xaa is an Independently selected amino
      acid
<220> FEATURE:
<221> NAME/KEY: MOD_RES
<222> LOCATION: (7)
<223> OTHER INFORMATION: Where Xaa is an independently selected amino
      acid
<220> FEATURE:
<221> NAME/KEY: MOD_RES
<222> LOCATION: (8)
<223> OTHER INFORMATION: Where Xaa is either Serine or Threonine

<400> SEQUENCE: 10

Xaa Phe Xaa Xaa Xaa Xaa Xaa Xaa Gly
 1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 11

Ile Asp Asp Lys
```

```
<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 12

Asp Asp Lys Ser
  1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 13

Val Ile Asp Asp Lys
  1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 14

Ile Asp Asp Lys Ser
  1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 15

Val Ile Asp Asp Lys Ser
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 16

Asp Asp Lys Ser Gly
  1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Product of
```

Synthesis based on Human OB-Cadherin

<400> SEQUENCE: 17

Ile Asp Asp Lys Ser Gly
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 18

Val Ile Asp Asp Lys Ser Gly
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 19

Phe Val Ile Asp Asp Lys
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 20

Phe Val Ile Asp Asp Lys Ser
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 21

Phe Val Ile Asp Asp Lys Ser Gly
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 22

Ile Phe Val Ile Asp Asp Lys
 1               5

<210> SEQ ID NO 23

```
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 23

Ile Phe Val Ile Asp Asp Lys Ser
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 24

Ile Phe Val Ile Asp Asp Lys Ser Gly
 1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 25

Ile Glu Glu Tyr
 1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 26

Glu Glu Tyr Thr
 1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 27

Val Ile Glu Glu Tyr
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 28
```

-continued

```
Ile Glu Glu Tyr Thr
  1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 29

Val Ile Glu Glu Tyr Thr
  1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 30

Glu Glu Tyr Thr Gly
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 31

Ile Glu Glu Tyr Thr Gly
  1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 32

Val Ile Glu Glu Tyr Thr Gly
  1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 33

Phe Val Ile Glu Glu Tyr
  1               5

<210> SEQ ID NO 34
<211> LENGTH: 7
<212> TYPE: PRT
<213> ORGANISM: Artificial Sequence
<220> FEATURE:
```

```
<223> OTHER INFORMATION: Description of Artificial Sequence:  Product of
      Synthesis based on Human OB-Cadherin

<400> SEQUENCE: 34

Phe Val Ile Glu Glu Tyr Thr
  1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 35

Phe Val Ile Glu Glu Tyr Thr Gly
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 36

Phe Phe Val Ile Glu Glu Tyr
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 37

Phe Phe Val Ile Glu Glu Tyr Thr
  1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 38

Phe Phe Val Ile Glu Glu Tyr Thr Gly
  1               5

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 39

Val Glu Ala Gln
  1
```

```
<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 40

Glu Ala Gln Thr
  1

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 41

Ser Val Glu Ala Gln
  1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 42

Val Glu Ala Gln Thr
  1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 43

Ser Val Glu Ala Gln Thr
  1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 44

Glu Ala Gln Thr Gly
  1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on Human OB-Cadherin

<400> SEQUENCE: 45
```

```
Val Glu Ala Gln Thr Gly
  1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 46

Ser Val Glu Ala Gln Thr Gly
  1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 47

Phe Ser Val Glu Ala Gln
  1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 48

Phe Ser Val Glu Ala Gln Thr
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 49

Phe Ser Val Glu Ala Gln Thr Gly
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 50

Tyr Phe Ser Val Glu Ala Gln
  1               5

<210> SEQ ID NO 51
<211> LENGTH: 8
<212> TYPE: PRT
<213> ORGANISM: Artificial Sequence
```

```
<220> FEATURE:
<223> OTHER INFORMATION: Description of Artificial Sequence:  Product of
      Synthesis based on Human OB-Cadherin

<400> SEQUENCE: 51

Tyr Phe Ser Val Glu Ala Gln Thr
 1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin

<400> SEQUENCE: 52

Tyr Phe Ser Val Glu Ala Gln Thr Gly
 1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis based on Human OB-Cadherin
<220> FEATURE:
<221> NAME/KEY: MOD_RES
<222> LOCATION: (1)
OTHER INFORMATION: ACETYLATION
FEATURE:
<221> NAME/KEY: MOD_RES
<222> LOCATION: (9)
<223> OTHER INFORMATION: AMIDATION

<400> SEQUENCE: 53

Phe Phe Val Ile Glu Glu Tyr Thr Gly
 1               5

<210> SEQ ID NO 54
<211> LENGTH: 9
TYPE: PRT
ORGANISM: Artificial Sequence
<220> FEATURE:
<223> OTHER INFORMATION: Description of Artificial Sequence:  Product of
      Synthesis based on Human OB-Cadherin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (9)
<223> OTHER INFORMATION: AMIDATION

<400> SEQUENCE: 54

Tyr Phe Ser Val Glu Ala Gln Thr Gly
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide
```

```
<400> SEQUENCE: 55

Cys Asp Asp Lys Cys
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 56

Cys Ile Asp Asp Lys Cys
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 57

Cys Asp Asp Lys Ser Cys
 1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 58

Cys Val Ile Asp Asp Lys Cys
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 59

Cys Ile Asp Asp Lys Ser Cys
 1               5

<210> SEQ ID NO 60
<211> LENGTH: 8
<212> TYPE: PRT
<213> ORGANISM: Artificial Sequence
<220> FEATURE:
```

```
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 60

Cys Val Ile Asp Asp Lys Ser Cys
  1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 61

Cys Asp Asp Lys Ser Gly Cys
  1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 62

Cys Ile Asp Asp Lys Ser Gly Cys
  1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 63

Cys Val Ile Asp Asp Lys Ser Gly Cys
  1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 64

Cys Phe Val Ile Asp Asp Lys Cys
  1               5
```

```
<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 65

Cys Phe Val Ile Asp Asp Lys Ser Cys
 1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 66

Cys Phe Val Ile Asp Asp Lys Ser Gly Cys
 1               5                  10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 67

Cys Ile Phe Val Ile Asp Asp Lys Cys
 1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 68

Cys Ile Phe Val Ile Asp Asp Lys Ser Cys
 1               5                  10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide
```

<400> SEQUENCE: 69

Cys Ile Phe Val Ile Asp Asp Lys Ser Gly Cys
 1               5                  10

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 70

Asp Asp Asp Lys Lys
 1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 71

Asp Ile Asp Asp Lys Lys
 1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 72

Asp Val Ile Asp Asp Lys Lys
 1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 73

Asp Phe Val Ile Asp Asp Lys Lys
 1               5

<210> SEQ ID NO 74
<211> LENGTH: 9
<212> TYPE: PRT
<213> ORGANISM: Artificial Sequence

```
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 74

Asp Ile Phe Val Ile Asp Asp Lys Lys
  1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 75

Glu Asp Asp Lys Lys
  1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 76

Glu Ile Asp Asp Lys Lys
  1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 77

Glu Val Ile Asp Asp Lys Lys
  1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 78

Glu Phe Val Ile Asp Asp Lys Lys
  1               5
```

```
<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 79

Glu Ile Phe Val Ile Asp Asp Lys Lys
 1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 80

Phe Val Ile Asp Asp Lys
 1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 81

Phe Val Ile Asp Asp Lys Ser
 1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 82

Phe Val Ile Asp Asp Lys Ser Gly
 1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
```

<223> OTHER INFORMATION: Cyclic Peptide

<400> SEQUENCE: 83

Lys Asp Asp Lys Asp
 1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 84

Lys Ile Asp Asp Lys Asp
 1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 85

Lys Asp Asp Lys Ser Asp
 1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 86

Lys Val Ile Asp Asp Lys Asp
 1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 87

Lys Ile Asp Asp Lys Ser Asp
 1               5

<210> SEQ ID NO 88
<211> LENGTH: 8
<212> TYPE: PRT

```
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 88

Lys Val Ile Asp Asp Lys Ser Asp
  1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 89

Lys Asp Asp Lys Ser Gly Asp
  1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 90

Lys Ile Asp Asp Lys Ser Gly Asp
  1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 91

Lys Val Ile Asp Asp Lys Ser Gly Asp
  1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 92

Lys Phe Val Ile Asp Asp Lys Asp
```

```
                1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 93

Lys Phe Val Ile Asp Asp Lys Ser Asp
  1               5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 94

Lys Phe Val Ile Asp Asp Lys Ser Gly Asp
  1               5                  10

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 95

Lys Ile Phe Val Ile Asp Asp Lys Asp
  1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 96

Lys Ile Phe Val Ile Asp Asp Lys Ser Asp
  1               5                  10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
```

```
<220> FEATURE:
<223> OTHER INFORMATION: Cyclic Peptide

<400> SEQUENCE: 97

Lys Ile Phe Val Ile Asp Asp Lys Ser Gly Asp
 1               5                  10

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 98

Val Ile Asp Asp Lys
 1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 99

Ile Asp Asp Lys Ser
 1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 100

Val Ile Asp Asp Lys Ser
 1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 101

Val Ile Asp Asp Lys Ser Gly
 1               5

<210> SEQ ID NO 102
<211> LENGTH: 5
```

```
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 102

Asp Asp Lys Ser Gly
 1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 103

Ile Asp Asp Lys Ser Gly
 1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 104

Ile Phe Val Ile Asp Asp Lys
 1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 105

Ile Phe Val Ile Asp Asp Lys Ser
 1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 106
```

```
Ile Phe Val Ile Asp Asp Lys Ser Gly
 1               5
```

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 107

```
Lys Asp Asp Lys Glu
 1               5
```

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 108

```
Lys Ile Asp Asp Lys Glu
 1               5
```

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 109

```
Lys Asp Asp Lys Ser Glu
 1               5
```

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 110

```
Lys Val Ile Asp Asp Lys Glu
 1               5
```

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human

```
            OB-Cadherin
<220> FEATURE:
<223> OTHER INFORMATION: Cyclic Peptide

<400> SEQUENCE: 111

Lys Ile Asp Asp Lys Ser Glu
 1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 112

Lys Val Ile Asp Asp Lys Ser Glu
 1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 113

Lys Asp Asp Lys Ser Gly Glu
 1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 114

Lys Ile Asp Asp Lys Ser Gly Glu
 1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 115

Lys Val Ile Asp Asp Lys Ser Gly Glu
 1               5

<210> SEQ ID NO 116
```

```
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 116

Lys Phe Val Ile Asp Asp Lys Glu
  1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 117

Lys Phe Val Ile Asp Asp Lys Ser Glu
  1               5

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 118

Lys Phe Val Ile Asp Asp Lys Ser Gly Glu
  1               5                  10

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 119

Lys Ile Phe Val Ile Asp Asp Lys Glu
  1               5

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 120
```

-continued

```
Lys Ile Phe Val Ile Asp Asp Lys Ser Glu
 1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 121

Lys Ile Phe Val Ile Asp Asp Lys Ser Gly Glu
 1               5                   10

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 122

Cys Glu Glu Tyr Cys
 1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 123

Cys Ile Glu Glu Tyr Cys
 1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 124

Cys Glu Glu Tyr Thr Cys
 1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence:  Product of
```

```
        Synthesis and Cyclization based on Human
        OB-Cadherin
<220> FEATURE:
<223> OTHER INFORMATION: Cyclic Peptide

<400> SEQUENCE: 125

Cys Val Ile Glu Glu Tyr Cys
  1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 126

Cys Ile Glu Glu Tyr Thr Cys
  1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 127

Cys Val Ile Glu Glu Tyr Thr Cys
  1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 128

Cys Glu Glu Tyr Thr Gly Cys
  1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 129

Cys Ile Glu Glu Tyr Thr Gly Cys
  1               5
```

```
<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 130

Cys Val Ile Glu Glu Tyr Thr Gly Cys
  1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 131

Cys Phe Val Ile Glu Glu Tyr Cys
  1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 132

Cys Phe Val Ile Glu Glu Tyr Thr Cys
  1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 133

Cys Phe Val Ile Glu Glu Tyr Thr Gly Cys
  1               5                  10

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide
```

```
<400> SEQUENCE: 134

Cys Phe Phe Val Ile Glu Glu Tyr Cys
 1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 135

Cys Phe Phe Val Ile Glu Glu Tyr Thr Cys
 1               5                  10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 136

Cys Phe Phe Val Ile Glu Glu Tyr Thr Gly Cys
 1               5                  10

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 137

Lys Glu Glu Tyr Asp
 1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 138

Lys Ile Glu Glu Tyr Asp
 1               5

<210> SEQ ID NO 139
<211> LENGTH: 6
<212> TYPE: PRT
<213> ORGANISM: Artificial Sequence
<220> FEATURE:
```

```
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 139

Lys Glu Glu Tyr Thr Asp
 1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 140

Lys Val Ile Glu Glu Tyr Asp
 1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 141

Lys Ile Glu Glu Tyr Thr Asp
 1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 142

Lys Val Ile Glu Glu Tyr Thr Asp
 1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 143

Lys Glu Glu Tyr Thr Gly Cys Asp
 1               5
```

```
<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 144

Lys Ile Glu Glu Tyr Thr Gly Asp
 1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 145

Lys Val Ile Glu Glu Tyr Thr Gly Asp
 1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 146

Lys Phe Val Ile Glu Glu Tyr Asp
 1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 147

Lys Phe Val Ile Glu Glu Tyr Thr Asp
 1               5

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide
```

```
<400> SEQUENCE: 148

Lys Phe Val Ile Glu Glu Tyr Thr Gly Asp
 1               5                  10

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 149

Lys Phe Phe Val Ile Glu Glu Tyr Asp
 1               5

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 150

Lys Phe Phe Val Ile Glu Glu Tyr Thr Asp
 1               5                  10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 151

Lys Phe Phe Val Ile Glu Glu Tyr Thr Gly Asp
 1               5                  10

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 152

Glu Glu Glu Tyr Lys
 1               5

<210> SEQ ID NO 153
<211> LENGTH: 6
<212> TYPE: PRT
<213> ORGANISM: Artificial Sequence
```

```
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 153

Glu Ile Glu Glu Tyr Lys
 1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 154

Glu Glu Glu Tyr Thr Lys
 1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 155

Glu Val Ile Glu Glu Tyr Lys
 1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 156

Glu Ile Glu Glu Tyr Thr Lys
 1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 157

Glu Val Ile Glu Glu Tyr Thr Lys
 1               5
```

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 158

Glu Glu Glu Tyr Thr Gly Lys
  1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 159

Glu Ile Glu Glu Tyr Thr Gly Lys
  1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 160

Glu Val Ile Glu Glu Tyr Thr Gly Lys
  1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 161

Glu Phe Val Ile Glu Glu Tyr Lys
  1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:

<223> OTHER INFORMATION: Cyclic Peptide

<400> SEQUENCE: 162

Glu Phe Val Ile Glu Glu Tyr Thr Lys
 1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 163

Glu Phe Val Ile Glu Glu Tyr Thr Gly Lys
 1               5                  10

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 164

Glu Phe Phe Val Ile Glu Glu Tyr Lys
 1               5

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 165

Glu Phe Phe Val Ile Glu Glu Tyr Thr Lys
 1               5                  10

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 166

Glu Phe Phe Val Ile Glu Glu Tyr Thr Gly Lys
 1               5                  10

<210> SEQ ID NO 167
<211> LENGTH: 6
<212> TYPE: PRT

```
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 167

Asp Cys Glu Glu Tyr Lys
  1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 168

Asp Ile Glu Glu Tyr Cys Lys
  1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 169

Asp Glu Glu Tyr Thr Lys
  1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 170

Asp Val Ile Glu Glu Tyr Lys
  1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 171

Asp Ile Glu Glu Tyr Thr Lys
```

-continued

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 172

Asp Val Ile Glu Glu Tyr Thr Lys
  1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 173

Asp Glu Glu Tyr Thr Gly Lys
  1               5

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 174

Asp Ile Glu Glu Tyr Thr Gly Lys
  1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 175

Asp Val Ile Glu Glu Tyr Thr Gly Lys
  1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin

```
<220> FEATURE:
<223> OTHER INFORMATION: Cyclic Peptide

<400> SEQUENCE: 176

Asp Phe Val Ile Glu Glu Tyr Lys
 1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 177

Asp Phe Val Ile Glu Glu Tyr Thr Lys
 1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 178

Asp Phe Val Ile Glu Glu Tyr Thr Gly Lys
 1               5                  10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 179

Asp Phe Phe Val Ile Glu Glu Tyr Lys
 1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 180

Asp Phe Phe Val Ile Glu Glu Tyr Thr Lys
 1               5                  10

<210> SEQ ID NO 181
<211> LENGTH: 11
```

```
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 181

Asp Phe Phe Val Ile Glu Glu Tyr Thr Gly Lys
  1               5                  10

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 182

Lys Glu Glu Tyr Glu
  1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 183

Lys Ile Glu Glu Tyr Glu
  1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 184

Lys Glu Glu Tyr Thr Glu
  1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 185
```

```
Lys Val Ile Glu Glu Tyr Glu
 1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 186

Lys Ile Glu Glu Tyr Thr Glu
 1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 187

Lys Val Ile Glu Glu Tyr Thr Glu
 1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 188

Lys Glu Glu Tyr Thr Gly Glu
 1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 189

Lys Ile Glu Glu Tyr Thr Gly Glu
 1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
```

```
            OB-Cadherin
<220> FEATURE:
<223> OTHER INFORMATION: Cyclic Peptide

<400> SEQUENCE: 190

Lys Val Ile Glu Glu Tyr Thr Gly Glu
  1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 191

Lys Phe Val Ile Glu Glu Tyr Glu
  1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 192

Lys Phe Val Ile Glu Glu Tyr Thr Glu
  1               5

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 193

Lys Phe Val Ile Glu Glu Tyr Thr Gly Glu
  1               5                  10

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 194

Lys Phe Phe Val Ile Glu Glu Tyr Glu
  1               5

<210> SEQ ID NO 195
```

```
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 195

Lys Phe Phe Val Ile Glu Glu Tyr Thr Glu
 1               5                  10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 196

Lys Phe Phe Val Ile Glu Glu Tyr Thr Gly Glu
 1               5                  10

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 197

Val Ile Glu Glu Tyr
 1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 198

Ile Glu Glu Tyr Thr
 1               5

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 199
```

```
Val Ile Glu Glu Tyr Thr
 1               5
```

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 200

```
Glu Glu Tyr Thr Gly
 1               5
```

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 201

```
Ile Glu Glu Tyr Thr Gly
 1               5
```

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 202

```
Val Ile Glu Glu Tyr Thr Gly
 1               5
```

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 203

```
Phe Val Ile Glu Glu Tyr
 1               5
```

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence:  Product of

```
        Synthesis and Cyclization based on Human
        OB-Cadherin
<220> FEATURE:
<223> OTHER INFORMATION: Cyclic Peptide

<400> SEQUENCE: 204

Phe Val Ile Glu Glu Tyr Thr
  1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 205

Phe Val Ile Glu Glu Tyr Thr Gly
  1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 206

Phe Phe Val Ile Glu Glu Tyr
  1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 207

Phe Phe Val Ile Glu Glu Tyr Thr
  1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence:  Product of
        Synthesis and Cyclization based on Human
        OB-Cadherin
<220> FEATURE:
<223> OTHER INFORMATION: Cyclic Peptide

<400> SEQUENCE: 208

Phe Phe Val Ile Glu Glu Tyr Thr Gly
  1               5
```

```
<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 209

Cys Glu Ala Gln Cys
 1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 210

Cys Val Glu Ala Gln Cys
 1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 211

Cys Glu Ala Gln Thr Cys
 1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 212

Cys Ser Val Glu Ala Gln Cys
 1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide
```

```
<400> SEQUENCE: 213

Cys Val Glu Ala Gln Thr Cys
  1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 214

Cys Ser Val Glu Ala Gln Thr Cys
  1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 215

Cys Glu Ala Gln Thr Gly Cys
  1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 216

Cys Val Glu Ala Gln Thr Gly Cys
  1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 217

Cys Ser Val Glu Ala Gln Thr Gly Cys
  1               5

<210> SEQ ID NO 218
<211> LENGTH: 8
<212> TYPE: PRT
<213> ORGANISM: Artificial Sequence
<220> FEATURE:
```

```
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 218

Cys Phe Ser Val Glu Ala Gln Cys
  1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 219

Cys Phe Ser Val Glu Ala Gln Thr Cys
  1               5

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 220

Cys Phe Ser Val Glu Ala Gln Thr Gly Cys
  1               5                  10

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 221

Cys Tyr Phe Ser Val Glu Ala Gln Cys
  1               5

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 222

Cys Tyr Phe Ser Val Glu Ala Gln Thr Cys
  1               5                  10
```

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Product of
    Synthesis and Cyclization based on Human
    OB-Cadherin
<220> FEATURE:
<223> OTHER INFORMATION: Cyclic Peptide

<400> SEQUENCE: 223

Cys Tyr Phe Ser Val Glu Ala Gln Thr Gly Cys
 1               5                  10

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Product of
    Synthesis and Cyclization based on Human
    OB-Cadherin
<220> FEATURE:
<223> OTHER INFORMATION: Cyclic Peptide

<400> SEQUENCE: 224

Lys Glu Ala Gln Asp
 1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Product of
    Synthesis and Cyclization based on Human
    OB-Cadherin
<220> FEATURE:
<223> OTHER INFORMATION: Cyclic Peptide

<400> SEQUENCE: 225

Lys Val Glu Ala Gln Asp
 1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Product of
    Synthesis and Cyclization based on Human
    OB-Cadherin
<220> FEATURE:
<223> OTHER INFORMATION: Cyclic Peptide

<400> SEQUENCE: 226

Lys Glu Ala Gln Thr Asp
 1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Product of
    Synthesis and Cyclization based on Human
    OB-Cadherin
<220> FEATURE:
<223> OTHER INFORMATION: Cyclic Peptide

```
<400> SEQUENCE: 227

Lys Ser Val Glu Ala Gln Asp
  1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 228

Lys Val Glu Ala Gln Thr Asp
  1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 229

Lys Ser Val Glu Ala Gln Thr Asp
  1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 230

Lys Glu Ala Gln Thr Gly Asp
  1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 231

Lys Val Glu Ala Gln Thr Gly Asp
  1               5

<210> SEQ ID NO 232
<211> LENGTH: 9
<212> TYPE: PRT
<213> ORGANISM: Artificial Sequence
```

```
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 232

Lys Ser Val Glu Ala Gln Thr Gly Asp
  1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 233

Lys Phe Ser Val Glu Ala Gln Asp
  1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 234

Lys Phe Ser Val Glu Ala Gln Thr Asp
  1               5

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 235

Lys Phe Ser Val Glu Ala Gln Thr Gly Asp
  1               5                  10

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 236

Lys Tyr Phe Ser Val Glu Ala Gln Asp
  1               5
```

```
<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 237

Lys Tyr Phe Ser Val Glu Ala Gln Thr Asp
 1               5                  10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 238

Lys Tyr Phe Ser Val Glu Ala Gln Thr Gly Asp
 1               5                  10

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 239

Glu Glu Ala Gln Lys
 1               5

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 240

Glu Val Glu Ala Gln Lys
 1               5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
```

```
<223> OTHER INFORMATION: Cyclic Peptide

<400> SEQUENCE: 241

Glu Glu Ala Gln Thr Lys
 1               5

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 242

Glu Ser Val Glu Ala Gln Lys
 1               5

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 243

Glu Val Glu Ala Gln Thr Lys
 1               5

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 244

Glu Ser Val Glu Ala Gln Thr Lys
 1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 245

Glu Glu Ala Gln Thr Gly Lys
 1               5

<210> SEQ ID NO 246
<211> LENGTH: 8
<212> TYPE: PRT
```

```
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 246

Glu Val Glu Ala Gln Thr Gly Lys
  1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 247

Glu Ser Val Glu Ala Gln Thr Gly Lys
  1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 248

Glu Phe Ser Val Glu Ala Gln Lys
  1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 249

Glu Phe Ser Val Glu Ala Gln Thr Lys
  1               5

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 250

Glu Phe Ser Val Glu Ala Gln Thr Gly Lys
```

```
                    1               5                   10

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 251

Glu Tyr Phe Ser Val Glu Ala Gln Lys
  1               5

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 252

Glu Tyr Phe Ser Val Glu Ala Gln Thr Lys
  1               5                   10

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 253

Glu Tyr Phe Ser Val Glu Ala Gln Thr Gly Lys
  1               5                   10

<210> SEQ ID NO 254
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 254

Asp Glu Ala Gln Lys
  1               5

<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
```

```
<220> FEATURE:
<223> OTHER INFORMATION: Cyclic Peptide

<400> SEQUENCE: 255

Asp Val Glu Ala Gln Lys
 1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 256

Asp Glu Ala Gln Thr Lys
 1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 257

Asp Ser Val Glu Ala Gln Lys
 1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 258

Asp Val Glu Ala Gln Thr Lys
 1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 259

Asp Ser Val Glu Ala Gln Thr Lys
 1               5

<210> SEQ ID NO 260
<211> LENGTH: 7
```

```
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 260

Asp Glu Ala Gln Thr Gly Lys
 1               5

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 261

Asp Val Glu Ala Gln Thr Gly Lys
 1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 262

Asp Ser Val Glu Ala Gln Thr Gly Lys
 1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 263

Asp Phe Ser Val Glu Ala Gln Lys
 1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 264
```

Asp Phe Ser Val Glu Ala Gln Thr Lys
 1               5

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 265

Asp Phe Ser Val Glu Ala Gln Thr Gly Lys
 1               5                   10

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 266

Asp Tyr Phe Ser Val Glu Ala Gln Lys
 1               5

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 267

Asp Tyr Phe Ser Val Glu Ala Gln Thr Lys
 1               5                   10

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 268

Asp Tyr Phe Ser Val Glu Ala Gln Thr Gly Lys
 1               5                   10

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human

```
            OB-Cadherin
<220> FEATURE:
<223> OTHER INFORMATION: Cyclic Peptide

<400> SEQUENCE: 269

Lys Glu Ala Gln Glu
  1               5

<210> SEQ ID NO 270
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 270

Lys Val Glu Ala Gln Glu
  1               5

<210> SEQ ID NO 271
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 271

Lys Glu Ala Gln Thr Glu
  1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 272

Lys Ser Val Glu Ala Gln Glu
  1               5

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 273

Lys Val Glu Ala Gln Thr Glu
  1               5

<210> SEQ ID NO 274
```

```
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 274

Lys Ser Val Glu Ala Gln Thr Glu
 1               5

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 275

Lys Glu Ala Gln Thr Gly Glu
 1               5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 276

Lys Val Glu Ala Gln Thr Gly Glu
 1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 277

Lys Ser Val Glu Ala Gln Thr Gly Glu
 1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 278
```

Lys Phe Ser Val Glu Ala Gln Glu
  1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 279

Lys Phe Ser Val Glu Ala Gln Thr Glu
  1               5

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 280

Lys Phe Ser Val Glu Ala Gln Thr Gly Glu
  1               5                  10

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 281

Lys Tyr Phe Ser Val Glu Ala Gln Glu
  1               5

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      OB-Cadherin
<220> FEATURE:
<223> OTHER INFORMATION: Cyclic Peptide

<400> SEQUENCE: 282

Lys Tyr Phe Ser Val Glu Ala Gln Thr Glu
  1               5                  10

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence:  Product of

```
        Synthesis and Cyclization based on Human
        OB-Cadherin
<220> FEATURE:
<223> OTHER INFORMATION: Cyclic Peptide

<400> SEQUENCE: 283

Lys Tyr Phe Ser Val Glu Ala Gln Thr Gly Glu
 1               5                  10

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Product of
        Synthesis and Cyclization based on Human
        OB-Cadherin
<220> FEATURE:
<223> OTHER INFORMATION: Cyclic Peptide

<400> SEQUENCE: 284

Ser Val Glu Ala Gln
 1               5

<210> SEQ ID NO 285
<211> LENGTH: 5
<212> TYPE: PRT
<213> ORGANISM: Artificial Sequence
<220> FEATURE:
<223> OTHER INFORMATION: Description of Artificial Sequence: Product of
        Synthesis and Cyclization based on Human
        OB-Cadherin
<220> FEATURE:
<223> OTHER INFORMATION: Cyclic Peptide

<400> SEQUENCE: 285

Val Glu Ala Gln Thr
 1               5

<210> SEQ ID NO 286
<211> LENGTH: 6
<212> TYPE: PRT
<213> ORGANISM: Artificial Sequence
<220> FEATURE:
<223> OTHER INFORMATION: Description of Artificial Sequence: Product of
        Synthesis and Cyclization based on Human
        OB-Cadherin
<220> FEATURE:
<223> OTHER INFORMATION: Cyclic Peptide

<400> SEQUENCE: 286

Ser Val Glu Ala Gln Thr
 1               5

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Product of
        Synthesis and Cyclization based on Human
        OB-Cadherin
<220> FEATURE:
<223> OTHER INFORMATION: Cyclic Peptide

<400> SEQUENCE: 287

Glu Ala Gln Thr Gly
 1               5
```

```
<210> SEQ ID NO 288
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 288

Val Glu Ala Gln Thr Gly
 1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 289

Ser Val Glu Ala Gln Thr Gly
 1               5

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 290

Phe Ser Val Glu Ala Gln
 1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 291

Phe Ser Val Glu Ala Gln Thr
 1               5

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide
```

```
<400> SEQUENCE: 292

Phe Ser Val Glu Ala Gln Thr Gly
 1               5

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 293

Tyr Phe Ser Val Glu Ala Gln
 1               5

<210> SEQ ID NO 294
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 294

Tyr Phe Ser Val Glu Ala Gln Thr
 1               5

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      OB-Cadherin
<220> FEATURE:
<223> OTHER INFORMATION: Cyclic Peptide

<400> SEQUENCE: 295

Tyr Phe Ser Val Glu Ala Gln Thr Gly
 1               5

<210> SEQ ID NO 296
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      N-Cadherin
<220> FEATURE:
<223> OTHER INFORMATION: Cyclic Peptide

<400> SEQUENCE: 296

Cys His Ala Val Cys
 1               5

<210> SEQ ID NO 297
<211> LENGTH: 6
<212> TYPE: PRT
<213> ORGANISM: Artificial Sequence
<220> FEATURE:
```

```
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 297

Cys His Ala Val Asp Cys
  1               5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 298

Cys Ala His Ala Val Cys
  1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 299

Cys Ala His Ala Val Asp Cys
  1               5

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 300

Cys Ala His Ala Val Asp Ile Cys
  1               5

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 301

Cys Arg Ala His Ala Val Asp Cys
  1               5
```

```
<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      N-Cadherin
<220> FEATURE:
<223> OTHER INFORMATION: Cyclic Peptide

<400> SEQUENCE: 302

Cys Leu Arg Ala His Ala Val Cys
 1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      N-Cadherin
<220> FEATURE:
<223> OTHER INFORMATION: Cyclic Peptide

<400> SEQUENCE: 303

Cys Leu Arg Ala His Ala Val Asp Cys
 1               5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      N-Cadherin
<220> FEATURE:
<223> OTHER INFORMATION: Cyclic Peptide

<400> SEQUENCE: 304

Cys Ser His Ala Val Cys
 1               5

<210> SEQ ID NO 305
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      N-Cadherin
<220> FEATURE:
<223> OTHER INFORMATION: Cyclic Peptide

<400> SEQUENCE: 305

Cys His Ala Val Ser Cys
 1               5

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis and Cyclization based on Human
      N-Cadherin
<220> FEATURE:
<223> OTHER INFORMATION: Cyclic Peptide
```

```
<400> SEQUENCE: 306

Cys Ser His Ala Val Ser Cys
  1               5

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 307

Cys Ser His Ala Val Ser Ser Cys
  1               5

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 308

Cys His Ala Val Ser Ser Cys
  1               5

<210> SEQ ID NO 309
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 309

Lys His Ala Val Asp
  1               5

<210> SEQ ID NO 310
<211> LENGTH: 5
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 310

Asp His Ala Val Lys
  1               5

<210> SEQ ID NO 311
<211> LENGTH: 5
<212> TYPE: PRT
<213> ORGANISM: Artificial Sequence
```

-continued

```
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 311

Lys His Ala Val Glu
  1               5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 312

Ala His Ala Val Asp Ile
  1               5

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 313

Ser His Ala Val Asp Ser Ser
  1               5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis and Cyclization based on Human
      N-Cadherin
<220> FEATURE:
<223> OTHER INFORMATION: Cyclic Peptide

<400> SEQUENCE: 314

Lys Ser His Ala Val Ser Ser Asp
  1               5

<210> SEQ ID NO 315
<211> LENGTH: 19
<212> TYPE: DNA
<213> ORGANISM: Artificial Sequence
<220> FEATURE:
<223> OTHER INFORMATION: Description of Artificial Sequence:  OB-Cadherin
      forward primer

<400> SEQUENCE: 315
accagatgtc tgtatcaga                                              19

SEQ ID NO 316
LENGTH: 21
```

```
<212> TYPE: DNA
<213> ORGANISM: Artificial Sequence
<220> FEATURE:
<223> OTHER INFORMATION: Description of Artificial Sequence: OB-Cadherin
      reverse primer

<400> SEQUENCE: 316
gtctcctggt catcatctgc a                                              21

<210> SEQ ID NO 317
<211> LENGTH: 20
<212> TYPE: DNA
<213> ORGANISM: Artificial Sequence
FEATURE:
OTHER INFORMATION: Description of Artificial Sequence:  OB-Cadherin
      forward primer

<400> SEQUENCE: 317
gccagacaca gttcttaagg                                                20

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence:  OB-Cadherin
      reverse primer

SEQUENCE: 318 atcaacctga gtatcagta                                                 19

<210> SEQ ID NO 319
<211> LENGTH: 25
<212> TYPE: DNA
<213> ORGANISM: Artificial Sequence
<220> FEATURE:
<223> OTHER INFORMATION: Description of Artificial Sequence:  Hypoxanthine
      phosphoribosyltransferase (HPRT)-specific forward
      primer

<400> SEQUENCE: 319
cctgctggat tacattaaag cactg                                          25

<210> SEQ ID NO 320
<211> LENGTH: 25
<212> TYPE: DNA
<213> ORGANISM: Artificial Sequence
<220> FEATURE:
<223> OTHER INFORMATION: Description of Artificial Sequence:  Hypoxanthine
      phosphoribosyltransferase (HPRT)-specific reverse
      primer

<400> SEQUENCE: 320
gtcaagggca tatccaacaa caaac                                          25

<210> SEQ ID NO 321
LENGTH: 22
TYPE: DNA
<213> ORGANISM: Artificial Sequence
<220> FEATURE:
<223> OTHER INFORMATION: Description of Artificial Sequence:  E-Cadherin
      forward primer

<400> SEQUENCE: 321
ccttccccca acacgtcccc cc                                             22

<210> SEQ ID NO 322
```

```
<211> LENGTH: 20
<212> TYPE: DNA
<213> ORGANISM: Artificial Sequence
<220> FEATURE:
OTHER INFORMATION: Description of Artificial Sequence:  E-Cadherin
reverse primer

<400> SEQUENCE: 322
tctccacctc cttcttcatc                                              20

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence:  N-Cadherin
      forward primer

<400> SEQUENCE: 323
caagagcttg tcacaatcag g                                            21

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence:  N-Cadherin
      reverse primer

<400> SEQUENCE: 324
catttggatc atccgcatc                                               19
```

METHODS FOR DIAGNOSING AND EVALUATING CANCER

CROSS-REFERENCE TO RELATED APPLICATIONS

This application is a continuation-in-part of U.S. patent application Ser. No. 09/187,859, filed Nov. 6, 1998 now U.S. Pat. No. 6,358,920; which is a continuation-in-part of U.S. patent application Ser. No. 09/073,040, filed May 5, 1998 now U.S. Pat. No. 6,472,367.

TECHNICAL FIELD

The present invention relates generally to methods for cancer diagnosis, and more particularly to the use of compounds that detect expression of OB-cadherin or N-cadherin for diagnosing and determining the metastatic potential of cancers such as breast, ovarian and prostate cancer, as well as leukemia.

BACKGROUND OF THE INVENTION

Cancer is a significant health problem throughout the world. Although advances have been made in detection and therapy of cancer, no vaccine or other universally successful method for prevention or treatment is currently available. For example, among women, breast and ovarian cancer are prevalent in the United States and other countries. Breast cancer, in particular, remains the second leading cause of cancer-related deaths in women, affecting more than 180, 000 women in the United States each year. For women in North America, the life-time odds of getting breast cancer are now one in eight. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100, 1994. However, it remains difficult to evaluate the metastatic potential of a cancer, and the high mortality observed in breast cancer patients indicates that improvements are needed in the diagnosis and management of the disease.

Prostate cancer is the most common form of cancer among males, with an estimated incidence of 30% in men over the age of 50. Human prostate cancer has the propensity to metastasize to bone. Treatment is commonly based on surgery and/or radiation therapy, but these methods are ineffective in a significant percentage of cases, and this prevalent disease is currently the second leading cause of cancer death among men in the U.S. To improve treatment of the disease, early diagnosis is critical, but prostate cancer remains difficult to detect accurately. Two prostate specific proteins, prostate specific antigen (PSA) and prostatic acid phosphatase (PAP), have been used for diagnosis, but techniques employing such proteins cannot provide complete diagnostic information. For example, PSA measurements not indicate the level of metastasis of a prostate cancer.

Although additional markers for prostate and other cancers continue to be discovered, there is presently no accurate method for evaluating the metastatic potential of these cancers. In order to improve cancer treatment and survival, techniques that permit a more accurate diagnosis are needed. The present invention fulfills these needs and further provides other related advantages.

SUMMARY OF THE INVENTION

Briefly stated, this invention provides compositions and methods for diagnosing cancer, such as breast, ovarian and prostate cancer, as well as leukemia. Certain methods provided herein employ binding agents, such as antibodies and fragments thereof, that specifically recognize OB-cadherin or N-cadherin. Other methods employ one or more polynucleotides capable of hybridizing to a polynucleotide encoding OB-cadherin or N-cadherin.

Within certain aspects, the present invention provides methods for determining the presence or absence of a cancer in a patient, comprising the steps of: (a) contacting a biological sample obtained from a patient with a binding agent that specifically binds to OB-cadherin or N-cadherin; and (b) detecting in the sample an amount of polypeptide that binds to the binding agent, relative to a predetermined cut-off value, and therefrom determining the presence or absence of a cancer in the patient.

Within further aspects, methods are provided for monitoring the progression of a cancer in a patient, comprising the steps of: (a) contacting a biological sample obtained from a patient at a first point in time with a binding agent that specifically binds to OB-cadherin or N-cadherin; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) to the amount detected in step (b) and therefrom monitoring the progression of the cancer in the patient.

Within other aspects, methods are provided for evaluating the metastatic potential of a cancer in a patient, comprising the steps of: (a) contacting a biological sample obtained from a patient afflicted with cancer with a binding agent that specifically binds to OB-cadherin or N-cadherin; and (b) detecting in the sample an amount of polypeptide that binds to the binding agent, relative to a predetermined cut-off value, and therefrom evaluating the metastatic potential of the cancer in the patient.

Kits for determining the presence or absence of a cancer in a patient are also provided. Such kits may comprise: (a) an antibody or antigen-binding fragment thereof that specifically binds to an OB-cadherin or N-cadherin CAR sequence; and (b) a detection reagent.

The present invention further provides methods for determining the presence or absence of a metastatic cancer in a patient, comprising the steps of: (a) contacting a biological sample obtained from a patient with an oligonucleotide that hybridizes to a polynucleotide encoding OB-cadherin or N-cadherin; and (b) detecting in the sample a level of a polynucleotide that hybridizes to the oligonucleotide, relative to a predetermined cut-off value, and therefrom determining the presence or absence of a metastatic cancer in the patient. Within certain embodiments, the amount of mRNA is detected via polymerase chain reaction using, for example, at least one oligonucleotide primer that hybridizes to a polynucleotide that encodes OB-cadherin or N-cadherin, or a complement of such a polynucleotide. Within other embodiments, the amount of mRNA is detected using a hybridization technique, employing an oligonucleotide probe that hybridizes to a polynucleotide that encodes OB-cadherin or N-cadherin, or a complement of such a polynucleotide. In a preferred embodiment, at least one of the oligonucleotide primers comprises at least about 10 contiguous nucleotides of a DNA molecule encoding OB-cadherin or N-cadherin.

In related aspects, methods are provided for monitoring progression of a cancer in a patient, comprising the steps of: (a) contacting a biological sample obtained from a patient with an oligonucleotide that hybridizes to a polynucleotide encoding OB-cadherin or N-cadherin; (b) detecting in the sample an amount of polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring progression of a cancer in the patient.

Within other aspects, methods are provided for evaluating the metastatic potential of a cancer in a patient, comprising the steps of: (a) contacting a biological sample obtained from a patient with an oligonucleotide that hybridizes to a polynucleotide encoding OB-cadherin or N-cadherin; and (b) detecting in the sample an amount of a polynucleotide that hybridizes to the oligonucleotide, relative to a predetermined cut-off value, and therefrom evaluating the metastatic potential of the cancer in the patient.

In related aspects, diagnostic kits comprising the above oligonucleotide probes or primers are provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 2 provides the amino acid sequences of representative mammalian OB-cadherin EC1 domains: human OB-cadherin (SEQ ID NO:4) and mouse OB-cadherin (SEQ ID NO:5).

FIG. 3 provides the amino acid sequences of mammalian classical cadherin EC1 domains: human N-cadherin (SEQ ID NO:6), mouse N-cadherin (SEQ ID NO:7) and cow N-cadherin (SEQ ID NO:8).

FIG. 4A shows the cells 24 hours after exposure to 100 µl water/1 ml culture medium (magnification 200×). FIGS. 4B and 4C show the cells 24 hours after exposure to 100 µL of a solution containing 10 mg/mL N-Ac-IFVIDDKSG-NH$_2$ (SEQ ID NO:9) per 1 mL culture medium (magnifications of 200× and 100×, respectively). Arrows indicate rounded cells.

DETAILED DESCRIPTION OF THE INVENTION

Figure 1A:
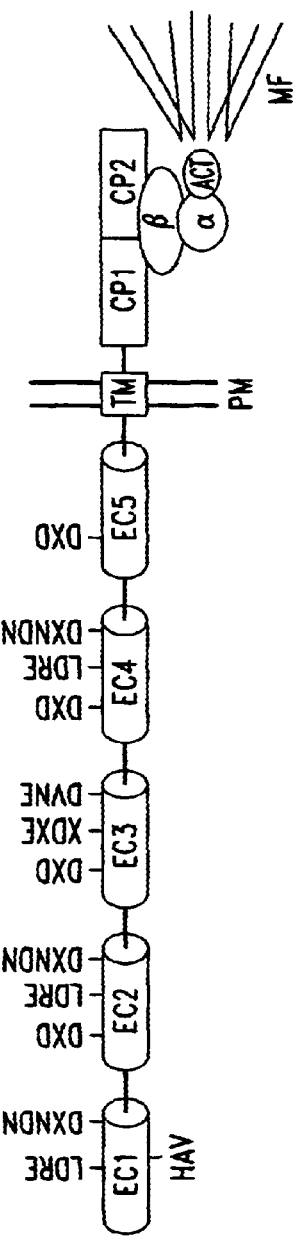
FIG. 1A is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:1), DXD and LDRE (SEQ ID NO:2). The CAR sequence, HAV, is shown within EC1. Cytoplasmic proteins β-catenin (β), α-catenin (α) and α-actinin (ACT), which mediate the interaction between CADs and microfilaments (MF) are also shown.
Figure 1B:
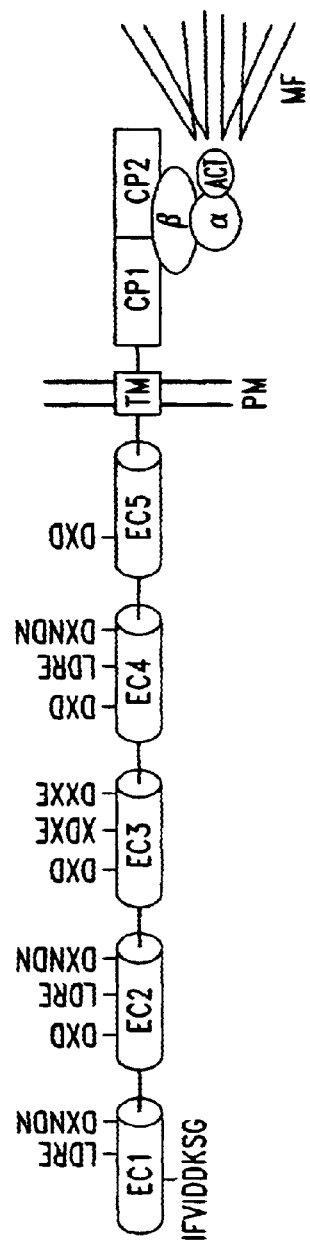
FIG. 1B is a diagram depicting the structure of the atypical CAD known as OB-cadherin. The CAR sequence, IFVIDDKSG (SEQ ID NO:3), is shown within EC1.

As noted above, the present invention provides methods for detecting and evaluating cancer in a patient. The methods provided herein are based, in part, on the discovery that OB-cadherin and N-cadherin are expressed by metastatic carcinoma cells, but not by highly differentiated, poorly invasive carcinomas. Accordingly, metastatic cancers may be detected and monitored using methods that evaluate OB-cadherin and/or N-cadherin expression. Certain methods provided herein employ binding agents, such as antibodies and fragments thereof, that specifically recognize an OB-cadherin or N-cadherin extracellular domain, or a portion thereof. Other methods employ one or more polynucleotides that hybridize to a polynucleotide encoding OB-cadherin or N-cadherin, or to a sequence that is a complement of such a polynucleotide. In general, within the methods provided herein, a biological sample obtained from a patient is typically contacted with such a binding agent or polynucleotide so as to permit determination of the level of OB-cadherin or N-cadherin, or the level of polynucleotide encoding OB-cadherin or N-cadherin. within the sample. This determination is indicative of the presence or absence of a metastatic cancer, and may be used to evaluate the metastatic potential of a cancer and monitor cancer progression.

OB-cadherin and N-Caderin

As used herein, the terms "OB-cadherin" and "N-cadherin" refer to cell adhesion molecules that are expressed by a human or non-human individual, and that are substantially homologous to a known OB-cadherin or N-cadherin (OB-cadherin and N-cadherin are discussed, for example, in Munro et al., In: *Cell Adhesion and Invasion in Cancer Metastasis*, P. Brodt, ed., pp. 17–34, RG Landes Co., Austin Tex., 1996; OB-cadherin is also described by Getsios et al., *Developmental Dynamics* 211:238–247, 1988; Simonneau et al., *Cell Adhesion and Communication* 3:115–130, 1995; Okazaki et al., *J. Biological Chemistry* 269:12092–12098, 1994). Certain OB-cadherin molecules comprise a sequence provided in FIG. 2 and certain N-cadherin molecules comprise a sequence provided in FIG. 3, but the present invention also contemplates the use of OB-cadherin and N-cadherin sequences from other organisms. Such OB-cadherin and N-cadherin sequences may generally be identified based upon sequence similarity to the sequences provided herein and based upon the presence of OB-cadherin or N-cadherin activity, using an assay provided herein.

For generating and testing binding agents, as described herein, polypeptides comprising a portion of OB-cadherin or N-cadherin may be used. Such polypeptides may, if they comprise a cell adhesion recognition sequence (CAR sequence), also be used as binding agents themselves. Preferred portions are extracellular domains and portions thereof, such as a portion comprising a CAR sequence. An extracellular domain of an OB-cadherin or N-cadherin may generally be identified based on homology to the extracellular domain sequences provided herein, and using well known techniques, such as the presence of one or more of: a hydrophilic sequence, a region that is recognized by an antibody, a region that is cleaved by trypsin and/or a potential glycosylation site with the glycosylation motif Asn-X-Ser/Thr. A polypeptide may comprise an entire extracellular domain or a portion thereof, and may consist entirely of the OB-cadherin or N-cadherin sequence, or may additionally comprise further peptide and/or non-peptide regions. Additional peptide regions may be derived from OB-cadherin or N-cadherin and/or may be heterologous. Such a peptide may be a linear or cyclic peptide, cyclized via an intramolecular bond that may be backbone to backbone, side-chain to backbone or side-chain to side-chain.

Polypeptides comprising an OB-cadherin or N-cadherin sequence may be synthesized by methods well known in the art, including chemical synthesis and recombinant DNA methods. For peptides up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first amino acid and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

If desired, acetylation of the N-terminus can be accomplished by reacting the final peptide with acetic anhydride before cleavage from the resin. C-amidation is accomplished using an appropriate resin such as methylbenzhydrylamine resin using the Boc technology. Following synthesis of a linear peptide, with or without N-acetylation and/or C-amidation, cyclization may be achieved, if desired, by any of a variety of techniques well known in the art.

For longer polypeptides, recombinant methods are preferred for synthesis. Within such methods, all or part of a polypeptide can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may be prepared based on known cDNA or genomic sequences, or from sequences isolated by screening an appropriate library with probes designed based on the sequences of known nonclassical cadherins. Such screens may generally be performed as described in Sambrook et al., *Molecular Cloning: A Laboratory Manual,* Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired polypeptide, an endogenous OB-cadherin or N-cadherin sequence may be modified using well known techniques. Alternatively, portions of the desired nucleic acid sequences may be synthesized using well known techniques, and then ligated together to form a sequence encoding the polypeptide.

Proteins and peptides may be evaluated for OB-cadherin or N-cadherin activity using any of a variety of assays. An initial screen for OB-cadherin or N-cadherin activity may be performed by evaluating the ability to bind to OB-cadherin or N-cadherin using any binding assay known to those of ordinary skill in the art. For example, a Pharmacia Biosensor machine may be used, as discussed in Jonsson et al., *Biotechniques* 11:520–27, 1991. A specific example of a technology that measures the interaction of peptides with molecules can be found in Williams et al., *J. Biol. Chem.* 272, 22349–22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 $\mu$g/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with OB-cadherin or N-cadherin derivatized to biotin. Any non-specifically bound protein is removed.

To determine binding, test analytes (e.g., peptides or proteins) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, OB-cadherin binds to an OB-cadherin extracellular domain (and N-cadherin binds to an N-cadherin extracellular domain) at a detectable level within such as assay.

OB-cadherin or N-cadherin activity may be evaluated using any of a variety of in vitro assays designed to measure the effect on a response that is mediated by OB-cadherin or N-cadherin. The ability to modulate cell adhesion may generally be evaluated in vitro by assaying the effect on adhesion between cells expressing OB-cadherin or N-cadherin. In general, a polypeptide is an inhibitor of cell adhesion if contact of the test cells with the polypeptide results in a discernible disruption of cell adhesion. Such assays may be performed using any type of cell that expresses OB-cadherin or N-cadherin at a detectable level, using standard techniques such as immunocytochemical protocols (e.g., Blaschuk and Farookhi, *Dev. Biol.* 136:564–567, 1989). For example, such cells may be plated under standard conditions that, in the absence of soluble OB-cadherin or N-cadherin, permit cell adhesion. In the presence of OB-cadherin or N-cadherin (e.g., 1 mg/mL), disruption of cell adhesion may be determined visually within 24 hours, by observing retraction of the cells from one another and the substratum.

Cells that express OB-cadherin include stromal, osteoblast and metastatic cancer cells. Cells that express N-cadherin include neural cells, endothelial cells and a variety of cancer cell types. Alternatively, cells that do not naturally express OB-cadherin or N-cadherin may be used within such assays. Such cells may be stably transfected with a polynucleotide (e.g., a cDNA) encoding OB-cadherin or N-cadherin, such that OB-cadherin or N-cadherin is expressed on the surface of the cell. Expression of OB-cadherin or N-cadherin may be confirmed by assessing adhesion of the transfected cells, in conjunction with immunocytochemical techniques using antibodies directed against OB-cadherin or N-cadherin. The stably transfected cells that aggregate, as judged by light microscopy, following transfection express sufficient levels of OB-cadherin or N-cadherin. Preferred cells for use in such assays include L cells, which do not detectably adhere and do not express any cadherin (Nagafuchi et al., *Nature* 329:341–343, 1987). Following transfection of L cells with a cDNA encoding OB-cadherin or N-cadherin, aggregation is observed (see Okazaki et al., *J. Biol. Chem.* 269:12092–98, 1994). Peptides that detectably inhibit such aggregation may be used to generate or characterize binding agents as described herein.

By way of example, an assay for evaluating the ability to inhibit an OB-cadherin mediated function may employ MDA-231 human breast cancer cells. According to a representative procedure, the cells may be plated at 10–20,000 cells per 35 mm tissue culture flasks containing DMEM with 5% FCS and sub-cultured periodically (Sommers et al., *Cell Growth Diffn* 2:365–72, 1991). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to a test compound (e.g., protein or peptide) at a concentration of, for example, 1 mg/mL for 24 hours. Fresh test compound may then be added, and the cells left for an additional 24 hours. Cells may be fixed with 2% paraformaldehyde for 30 minutes and then washed three times with PBS. Coverslips can be mounted and viewed by phase contrast microscopy.

In the absence of OB-cadherin or a portion thereof comprising a cell adhesion recognition sequence, MDA-231 cells display an epithelial-like morphology and are well attached to the substratum. MDA-231 cells that are treated with such a peptide or protein may assume a round shape and become loosely attached to the substratum within 48 hours of treatment with 1 mg/mL of OB-cadherin.

Alternatively, a protein or peptide may be assessed for the ability to enhance skin permeability. This ability may be assessed by determining, for example, the effect on permeability of adherent epithelial and/or endothelial cell layers (e.g., human skin). Such skin may be derived from a natural source or may be synthetic. Human abdominal skin for use in such assays may generally be obtained from humans at autopsy within 24 hours of death. Briefly, a test compound (e.g., 500 $\mu$g/ml) and a marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58–68, 1978; Franz, *J. Invest. Dermatol.* 64:190–195, 1975). The penetration of the markers through the skin may be assessed at, for example, 6, 12, 24, 36, and 48 hours after the start of the experiment. In general, OB-cadherin, N-cadherin or a portion thereof comprising a cell adhesion recognition sequence should result in a statistically significant increase in the amount of marker in the receptor compartment after 6–48 hours in the presence of 500 μg/mL peptide.

Yet another assay evaluates the ability to inhibit angiogenesis. The effect on angiogenesis may generally be determined by evaluating the effect on blood vessel formation. Such a determination may generally be performed, for example, using a chick chorioallantoic membrane assay (Iruela-Arispe et al., *Molecular Biology of the Cell* 6:327–343, 1995). Briefly, a peptide or protein may be embedded in a mesh composed of vitrogen at one or more concentrations (e.g., ranging from about 1 to 100 μg/mesh). The mesh(es) may then be applied to chick chorioallantoic membranes. After 24 hours, the effect may be determined using computer assisted morphometric analysis. OB-cadherin, N-cadherin or a portion thereof comprising a CAR sequence should inhibit angiogenesis by at least 25% at a concentration of 33 μg/mesh.

For N-cadherin, a neurite outgrowth assay may be used. Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; and Safell et al., *Neuron* 18:231–242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2%FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry. N-cadherin or a portion thereof comprising a cell adhesion recognition sequence (e.g., 500 μg/mL) should result in a decrease in the mean neurite length by at least 50%, relative to the length in the absence of such a polypeptide.

Binding Agents

The term "binding agent" refers to a substance such as a polypeptide comprising an OB-cadherin or N-cadherin CAR sequence, or antibody (or antigen-binding fragment thereof) that specifically binds to an OB-cadherin or N-cadherin. Certain preferred binding agents bind to an OB-cadherin or N-cadherin extracellular domain. As used herein, a substance is said to "specifically bind" to an OB-cadherin or N-cadherin sequence if it reacts at a detectable level with OB-cadherin or N-cadherin, and does not react detectably with peptides containing an unrelated sequence or a sequence of a different cadherin. Such binding properties may generally be assessed using an ELISA, which may be readily performed by those of ordinary skill in the art and is described, for example, by Newton et al., *Develop. Dynamics* 197:1–13, 1993. Each binding agent should satisfy the above criteria; however, those of ordinary skill in the art will recognize that binding agents may be used in combination to improve sensitivity. Peptides comprising OB-cadherin or N-cadherin sequences for use in preparing and evaluating binding agents may be generated as described herein.

Any compound that satisfies the above requirements may be a binding agent. For example, a binding agent may be a ribosome, with or without a peptide component, an RNA molecule or a polypeptide. Within certain preferred embodiments, a binding agent is a polypeptide that comprises an OB-cadherin or N-cadherin CAR sequence, a peptide variant thereof or a non-peptide mimetic of such a CAR sequence. As used herein, an "OB-cadherin CAR sequence" is a peptide portion of an OB-cadherin that is capable of modulating a function mediated by OB-cadherin. Similarly, an "N-cadherin CAR sequence" is a peptide portion of a N-cadherin that is capable of modulating a function mediated by N-cadherin. A CAR sequence may be of any length, but generally comprises at least three amino acid residues, preferably 4–16 amino acid residues and more preferably 5–9 amino acid residues. An N-cadherin CAR sequence generally comprises the peptide His-Ala-Val (HAV), with or without additional flanking sequence, which may be derived from the extracellular domain sequence provided in FIG. 3. Certain OB-cadherin CAR sequences have at least three consecutive amino acids present within the following consensus sequence in an OB-cadherin:

Aaa-Phe-Val/Ser-Ile/Val-Asp/Glu-Baa-Caa-Ser/Thr-Gly (SEQ ID NO:10)

wherein Aaa, Baa and Caa are independently selected amino acid residues; Val/Ser is an amino acid that is valine or serine; Ile/Val is an amino acid that is isoleucine or valine; Asp/Glu is an amino acid that is aspartate or glutamate; and Ser/Thr is an amino acid that is serine or threonine. Representative OB-cadherin CAR sequences include: DDK, IDDK (SEQ ID NO:11) DDKS (SEQ ID NO:12), VIDDK (SEQ ID NO:13), IDDKS (SEQ ID NO:14), VIDDKS (SEQ ID NO:15), DDKSG (SEQ ID NO:16), IDDKSG (SEQ ID NO:17), VIDDKSG (SEQ ID NO:18), FVIDDK (SEQ ID NO:19), FVIDDKS (SEQ ID NO:20), FVIDDKSG (SEQ ID NO:21), IFVIDDK (SEQ ID NO:22), IFVIDDKS (SEQ ID NO:23), IFVIDDKSG (SEQ ID NO:24), EEY, IEEY (SEQ ID NO:25), EEYT (SEQ ID NO:26), VIEEY (SEQ ID NO:27), IEEYT (SEQ ID NO:28), VIEEYT (SEQ ID NO:29), EEYTG (SEQ ID NO:30), IEEYTG (SEQ ID NO:31), VIEEYTG (SEQ ID NO:32), FVIEEY (SEQ ID NO:33), FVIEEYT (SEQ ID NO:34), FVIEEYTG (SEQ ID NO:35), FFVIEEY (SEQ ID NO:36), FFVIEEYT (SEQ ID NO:37), FFVIEEYTG (SEQ ID NO:38), EAQ, VEAQ (SEQ ID NO:39), EAQT (SEQ ID NO:40), SVEAQ (SEQ ID NO:41), VEAQT (SEQ ID NO:42), SVEAQT (SEQ ID NO:43), EAQTG (SEQ ID NO:44), VEAQTG (SEQ ID NO:45), SVEAQTG (SEQ ID NO:46), FSVEAQ (SEQ ID NO:47), FSVEAQT (SEQ ID NO:48), FSVEAQTG (SEQ ID NO:49), YFSVEAQ (SEQ ID NO:50), YFSVEAQT (SEQ ID NO:51) or YFSVEAQTG (SEQ ID NO:52). Linear peptides having such sequences may be modified at the N- and/or C-termini, as in the peptides N-Ac-IFVIDDKSG-NH$_2$ (SEQ ID NO:9), N-Ac-FFVIEEYTG-NH$_2$ (SEQ ID NO:53) and N-Ac-YFSVEAQTG-NH$_2$ (SEQ ID NO:54).

To confirm that a particular sequence is an OB-cadherin or N-cadherin CAR sequence, the ability of the sequence to modulate a function mediated by an OB-cadherin may be determined. For functions (e.g., cell adhesion) that are inhibited by a full length OB-cadherin or N-cadherin, a CAR sequence should inhibit the function with an activity that is not substantially diminished relative to the full length OB-cadherin or N-cadherin (i.e., the CAR sequence inhibits the function at least as well as soluble OB-cadherin or N-cadherin, when contacted with cells that express OB-cadherin or N-cadherin).

The present invention further contemplates the use of OB-cadherin and N-cadherin CAR sequences from other organisms. Such CAR sequences may be identified based upon similarity to the sequences provided herein, and the ability to modulate an OB-cadherin- or N-cadherin-mediated function may be confirmed as described herein.

As noted above, binding agents as described herein may comprise an analogue or mimetic of an OB-cadherin or N-cadherin CAR sequence. An analogue generally retains at least 50% identity to a native OB-cadherin or N-cadherin CAR sequence, and modulates an OB-cadherin- or N-cadherin-mediated function as described herein. Such analogues preferably contain at least three consecutive residues of, and more preferably at least five consecutive residues of, an OB-cadherin or N-cadherin CAR sequence. An analogue may contain any of a variety of amino acid substitutions, additions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of an OB-cadherin or N-cadherin CAR sequence analogue is the ability to modulate an OB-cadherin- or N-cadherin-mediated function, which may be evaluated using the representative assays provided herein.

A mimetic is a non-peptidyl compound that is conformationally similar to an OB-cadherin or N-cadherin CAR sequence, such that it modulates an OB-cadherin- or N-cadherin-mediated function as described herein. Such mimetics may be designed based on techniques that evaluate the three dimensional structure of a peptide. For example, Nuclear Magnetic Resonance spectroscopy (NMR) and computational techniques may be used to determine the conformation of a CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as $-CH_2NH-$, $-CSNH-$, $-CH_2S-$, $-CH=CH-$, $-CH_2CH_2-$, $-CONMe-$ and others. These backbone amide linkages can also be part of a ring structure (e.g., lactam). Mimetics may be designed where one or more of the side chain functionalities of a CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of a CAR sequence. It should be understood that, within embodiments described below, an analogue or mimetic may be substituted for an OB-cadherin or N-cadherin CAR sequence.

Binding agents, or peptide portions thereof, may be linear or cyclic peptides. The term "cyclic peptide," as used herein, refers to a peptide or salt thereof that comprises (1) an intramolecular covalent bond between two non-adjacent residues and (2) at least one OB-cadherin or N-cadherin CAR sequence or an analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds.

The size of a cyclic peptide ring generally ranges from 5 to about 15 residues, preferably from 5 to 10 residues. Additional residue(s) may be present on the N-terminal and/or C-terminal side of an OB-cadherin or N-cadherin CAR sequence, and may be derived from sequences that flank an OB-cadherin or N-cadherin CAR sequence, with or without amino acid substitutions and/or other modifications. Alternatively, additional residues present on one or both sides of the CAR sequence(s) may be unrelated to an endogenous sequence (e.g., residues that facilitate cyclization, purification or other manipulation and/or residues having a targeting or other function).

Within certain embodiments, a binding agent may comprise a cyclic peptide having the formula:

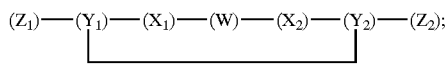

Within this formula, W is a tripeptide selected from the group consisting of EEY, DDK and EAQ (for OB-cadherin) or HAV (for N-cadherin); $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; $Y_1$ and $Y_2$ are independently selected from the group consisting of amino acid residues, and wherein a covalent bond is formed between residues $Y_1$ and $Y_2$; and $Z_1$ and $Z_2$ are optional, and if present, are independently selected from the group consisting of amino acid residues and combinations thereof in which the residues are linked by peptide bonds.

For example, representative cyclic peptides comprising an OB-cadherin CAR sequence include CDDKC (SEQ ID NO:55), CIDDKC (SEQ ID NO:56), CDDKSC (SEQ ID NO:57), CVIDDKC (SEQ ID NO:58), CIDDKSC (SEQ ID NO:59), CVIDDKSC (SEQ ID NO:60), CDDKSGC (SEQ ID NO:61), CIDDKSGC (SEQ ID NO:62), CVIDDKSGC (SEQ ID NO:63), CFVIDDKC (SEQ ID NO:64), CFVID- DKSC (SEQ ID NO:65), CFVIDDKSGC (SEQ ID NO:66), CIFVIDDKC (SEQ ID NO:67), CIFVIDDKSC (SEQ ID NO:68), CIFVIDDKSGC (SEQ ID NO:69), DDDKK (SEQ ID NO:70), DIDDKK (SEQ ID NO:71), DVIDDKK (SEQ ID NO:72), DFVIDDKK (SEQ ID NO:73), DIFVIDDKK (SEQ ID NO:74), EDDKK (SEQ ID NO:75), EIDDKK (SEQ ID NO:76), EVIDDKK (SEQ ID NO:77), EFVIDDKK (SEQ ID NO:78), EIFVIDDKK (SEQ ID NO:79), FVIDDK (SEQ ID NO:80), FVIDDKS (SEQ ID NO:81), FVIDDKSG (SEQ ID NO:82), KDDKD (SEQ ID NO:83), KIDDKD (SEQ ID NO:84), KDDKSD (SEQ ID NO:85), KVIDDKD (SEQ ID NO:86), KIDDKSD (SEQ ID NO:87), KVIDDKSD (SEQ ID NO:88), KDDKSGD (SEQ ID NO:89), KIDDKSGD (SEQ ID NO:90), KVIDDKSGD (SEQ ID NO:91), KFVIDDKD (SEQ ID NO:92), KFVIDDKSD (SEQ ID NO:93), KFVIDDKSGD (SEQ ID NO:94), KIFVIDDKD (SEQ ID NO:95), KIFVIDDKSD (SEQ ID NO:96), KIFVIDDKSGD (SEQ ID NO:97), VIDDK (SEQ ID NO:98), IDDKS (SEQ ID NO:99), VIDDKS (SEQ ID NO:100), VIDDKSG (SEQ ID NO:101), DDKSG (SEQ ID NO:102), IDDKSG (SEQ ID NO: 103), IFVIDDK (SEQ ID NO: 104), IFVIDDKS (SEQ ID NO: 105), IFVIDDKSG (SEQ ID NO:106), KDDKE (SEQ ID NO:107), KIDDKE (SEQ ID NO:108), KDDKSE (SEQ ID NO:109), KVIDDKE (SEQ ID NO:110), KIDDKSE (SEQ ID NO:111), KVIDDKSE (SEQ ID NO: 112), KDDKSGE (SEQ ID NO: 113), KIDDKSGE (SEQ ID NO: 114), KVIDDKSGE (SEQ ID NO: 115), KFVIDDKE (SEQ ID NO:116), KFVIDDKSE (SEQ ID NO:117), KFVIDDKSGE (SEQ ID NO:118), KIFVIDDKE (SEQ ID NO:119), KIFVIDDKSE (SEQ ID NO:120), KIFVIDDKSGE (SEQ ID NO: 121), CEEYC (SEQ ID NO: 122), CIEEYC (SEQ ID NO: 123), CEEYTC (SEQ ID NO:124), CVIEEYC (SEQ ID NO:125), CIEEYTC (SEQ ID NO:126), CVIEEYTC (SEQ ID NO:127), CEEYTGC (SEQ ID NO:128), CIEEYTGC (SEQ ID NO:129), CVIEEYTGC (SEQ ID NO:130), CFVIEEYC (SEQ ID NO:131), CFVIEEYTC (SEQ ID NO:132), CFVIEEYTGC (SEQ ID NO:133), CFFVIEEYC (SEQ ID NO:134), CFFVIEEYTC (SEQ ID NO:135), CFFVIEEYTGC (SEQ ID NO:136), KEEYD (SEQ ID NO:137), KIEEYD (SEQ ID NO:138), KEEYTD (SEQ ID NO:139), KVIEEYD (SEQ ID NO:140), KIEEYTD (SEQ ID NO:141), KVIEEYTD (SEQ ID NO:142), KEEYTGCD (SEQ ID NO:143), KIEEYTGD (SEQ ID NO:144), KVIEEYTGD (SEQ ID NO:145), KFVIEEYD (SEQ ID NO:146), KFVIEEYTD (SEQ ID NO:147), KFVIEEYTGD (SEQ ID NO:148), KFFVIEEYD (SEQ ID NO:149), KFFVIEEYTD (SEQ ID NO:150), KFFVIEEYTGD (SEQ ID NO:151), EEEYK (SEQ ID NO:152), EIEEYK (SEQ ID NO:153), EEEYTK (SEQ ID NO:154), EVIEEYK (SEQ ID NO:155), EIEEYTK (SEQ ID NO:156), EVIEEYTK (SEQ ID NO:157), EEEYTGK (SEQ ID NO:158), EIEEYTGK (SEQ ID NO:159), EVIEEYTGK (SEQ ID NO:160), EFVIEEYK (SEQ ID NO:161), EFVIEEYTK (SEQ ID NO:162), EFVIEEYTGK (SEQ ID NO:163), EFFVIEEYK (SEQ ID NO:164), EFFVIEEYTK (SEQ ID NO:165), EFFVIEEYTGK (SEQ ID NO: 166), DCEEYK (SEQ ID NO: 167), DIEEYCK (SEQ ID NO:168), DEEYTK (SEQ ID NO:169), DVIEEYK (SEQ ID NO:170), DIEEYTK (SEQ ID NO:171), DVIEEYTK (SEQ ID NO:172), DEEYTGK (SEQ ID NO:173), DIEEYTGK (SEQ ID NO:174), DVIEEYTGK (SEQ ID NO:175), DFVIEEYK (SEQ ID NO:176), DFVIEEYTK (SEQ ID NO:177), DFVIEEYTGK (SEQ ID NO:178), DFFVIEEYK (SEQ ID NO:179), DFFVIEEYTK (SEQ ID NO:180), DFFVIEEYTGK (SEQ ID NO:181), KEEYE (SEQ ID NO:182), KIEEYE (SEQ ID NO:183), KEEYTE (SEQ ID NO:184), KVIEEYE (SEQ ID NO:185), KIEEYTE (SEQ ID NO:186), KVIEEYTE (SEQ ID NO:187), KEEYTGE (SEQ ID NO:188), KIEEYTGE (SEQ ID NO:189), KVIEEYTGE (SEQ ID NO:190), KFVIEEYE (SEQ ID NO:191), KFVIEEYTE (SEQ ID NO: 192), KFVIEEYTGE (SEQ ID NO:193), KFFVIEEYE (SEQ ID NO:194), KFFVIEEYTE (SEQ ID NO:195), KFFVIEEYTGE (SEQ ID NO:196), VIEEY (SEQ ID NO:197), IEEYT (SEQ ID NO:198), VIEEYT (SEQ ID NO:199), EEYTG (SEQ ID NO:200), IEEYTG (SEQ ID NO:201), VIEEYTG (SEQ ID NO:202), FVIEEY (SEQ ID NO:203), FVIEEYT (SEQ ID NO:204), FVIEEYTG (SEQ ID NO:205), FFVIEEY (SEQ ID NO:206), FFVIEEYT (SEQ ID NO:207), FFVIEEYTG (SEQ ID NO:208), CEAQC (SEQ ID NO:209), CVEAQC (SEQ ID NO:210), CEAQTC (SEQ ID NO:211), CSVEAQC (SEQ ID NO:212), CVEAQTC (SEQ ID NO:213), CSVEAQTC (SEQ ID NO:214), CEAQTGC (SEQ ID NO:215), CVEAQTGC (SEQ ID NO:216), CSVEAQTGC (SEQ ID NO:217), CFSVEAQC (SEQ ID NO:218), CFSVEAQTC (SEQ ID NO:219), CFSVEAQTGC (SEQ ID NO:220), CYFSVEAQC (SEQ ID NO:221), CYFSVEAQTC (SEQ ID NO:222), CYFSVEAQTGC (SEQ ID NO:223), KEAQD (SEQ ID NO:224), KVEAQD (SEQ ID NO:225), KEAQTD (SEQ ID NO:226), KSVEAQD (SEQ ID NO:227), KVEAQTD (SEQ ID NO:228), KSVEAQTD (SEQ ID NO:229), KEAQTGD (SEQ ID NO:230), KVEAQTGD (SEQ ID NO:231), KSVEAQTGD (SEQ ID NO:232), KFSVEAQD (SEQ ID NO:233), KFSVEAQTD (SEQ ID NO:234), KFSVEAQTGD (SEQ ID NO:235), KYFSVEAQD (SEQ ID NO:236), KYFSVEAQTD (SEQ ID NO:237), KYFSVEAQTGD (SEQ ID NO:238), EEAQK (SEQ ID NO:239), EVEAQK (SEQ ID NO:240), EEAQTK (SEQ ID NO:241), ESVEAQK (SEQ ID NO:242), EVEAQTK (SEQ ID NO:243), ESVEAQTK (SEQ ID NO:244), EEAQTGK (SEQ ID NO:245), EVEAQTGK (SEQ ID NO:246), ESVEAQTGK (SEQ ID NO:247), EFSVEAQK (SEQ ID NO:248), EFSVEAQTK (SEQ ID NO:249), EFSVEAQTGK (SEQ ID NO:250), EYFSVEAOK (SEQ ID NO:251), EYFSVEAQTK (SEQ ID NO:252), EYFSVEAQTGK (SEQ ID NO:253), DEAQK (SEQ ID NO:254), DVEAQK (SEQ ID NO:255), DEAQTK (SEQ ID NO:256), DSVEAQTK (SEQ ID NO:257), DVEAQTK (SEQ ID NO:258), DSVEAQTK (SEQ ID NO:259), DEAQTGK (SEQ ID NO:260), DVEAQTGK (SEQ ID NO:261), DSVEAQTGK (SEQ ID NO:262), DFSVEAQK (SEQ ID NO:263), DFSVEAQTK (SEQ ID NO:264), DFSVEAQTGK (SEQ ID NO:265), DYFSVEAQK (SEQ ID NO:266), DYFSVEAQTK (SEQ ID NO:267), DYFSVEAQTGK (SEQ ID NO:268), KEAQE (SEQ ID NO:269), KVEAQE (SEQ ID NO:270), KEAQTE (SEQ ID NO:271), KSVEAQE (SEQ ID NO:272), KVEAQTE (SEQ ID NO:273), KSVEAQTE (SEQ ID NO:274), KEAQTGE (SEQ ID NO:275), KVEAQTGE (SEQ ID NO:276), KSVEAQTGE (SEQ ID NO:277), KFSVEAQE (SEQ ID NO:278), KFSVEAQTE (SEQ ID NO:279), KFSVEAQTGE (SEQ ID NO:280), KYFSVEAQE (SEQ ID NO:281), KYFSVEAQTE (SEQ ID NO:282), KYFSVEAQTGE (SEQ ID NO:283), SVEAQ (SEQ ID NO:284), VEAQT (SEQ ID NO:285), SVEAQT (SEQ ID NO:286), EAQTG (SEQ ID NO:287), VEAQTG (SEQ ID NO:288), SVEAQTG (SEQ ID NO:289), FSVEAQ (SEQ ID NO:290), FSVEAQT (SEQ ID NO:291), FSVEAQTG (SEQ ID NO:292), YFSVEAQ (SEQ ID NO:293), YFSVEAQT (SEQ ID NO:294) and YFSVEAQTG (SEQ ID NO:295). Within the context of the present invention, underlined sequences are cyclized using any suitable method, as described herein.

Representative cyclic peptides comprising an N-cadherin CAR sequence include CHAVC (SEQ ID NO:296), CHAVDC (SEQ ID NO:297), CAHAVC (SEQ ID NO:298), CAHAVDC (SEQ ID NO:299), CAHAVDIC (SEQ ID NO:300), CRAHAVDC (SEQ ID NO:301), CLRAHAVC (SEQ ID NO:302), CLRAHAVDC (SEQ ID NO:303), CSHAVC (SEQ ID NO:304), CHAVSC (SEQ ID NO:305), CSHAVSC (SEQ ID NO:306), CSHAVSSC (SEQ ID NO:307), CHAVSSC (SEQ ID NO:308), KHAVD (SEQ ID NO:309), DHAVK (SEQ ID NO:310), KHAVE (SEQ ID NO:311), AHAVDI (SEQ ID NO:312), SHAVDSS (SEQ ID NO:313) and KSHAVSSD (SEQ ID NO:314).

In certain other preferred embodiments, a binding agent is an antibody or an antigen-binding fragment thereof. Such antibodies may be polyclonal or monoclonal. In addition, the antibodies may be single chain, chimeric, CDR-grafted or humanized.

Polyclonal and monoclonal antibodies may be raised against an OB-cadherin or N-cadherin sequence using conventional techniques. See, e.g., Harlow and Lane, *Antibodies: A Laboratory Manual,* Cold Spring Harbor Laboratory, 1988. In one such technique, an immunogen comprising the sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the OB-cadherin or N-cadherin sequence may then be purified from such antisera by, for example, affinity chromatography using the OB-cadherin or N-cadherin sequence or antigenic portion thereof coupled to a suitable solid support.

Monoclonal antibodies specific for an OB-cadherin or N-cadherin sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the OB-cadherin or N-cadherin sequence or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

OB-cadherin and N-cadherin Polyneuclotides

A polynucleotide that encodes OB-cadherin or N-cadherin (or a portion or other variant thereof) or that is complementary to such a polynucleotide, may be used within certain methods provided herein. Polynucleotides may be single-stranded (coding or antisense) or double-stranded, and may be DNA (cDNA or synthetic) or RNA molecules. Additional coding or non-coding sequences may, but need not, be present within a polynucleotide of the present invention, and a polynucleotide may, but need not, be linked to other molecules and/or support materials. Oligonucleotides for use within the methods provided herein may be of any length suitable for the particular assay.

Polynucleotides may comprise a native sequence (i.e., an endogenous sequence that encodes OB-cadherin, N-cadherin or a portion thereof) or may comprise a variant of such a sequence. Polynucleotide variants preferably exhibit at least about 70% identity, more preferably at least about 80% identity and most preferably at least about 90% identity to a polynucleotide sequence that encodes a native OB-cadherin, N-cadherin or a portion thereof. Certain variants are substantially homologous to a native gene, or a portion or complement thereof. Such polynucleotide variants are capable of hybridizing under moderately stringent conditions to a naturally occurring DNA sequence encoding a native OB-cadherin or N-cadherin (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Polynucleotides may be prepared using any of a variety of techniques. For example, a polynucleotide may be amplified via polymerase chain reaction (PCR) from cDNA prepared from cells expressing OB-cadherin or N-cadherin. For this approach, sequence-specific primers may be designed based on the sequences provided herein, and may be purchased or synthesized. Other polynucleotides may be directly synthesized by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis. RNA molecules may be generated by in vitro or in vivo transcription of DNA sequences encoding OB-cadherin or N-cadherin, or portion thereof, provided that the DNA is incorporated into a vector with a suitable RNA polymerase promoter (such as T7 or SP6).

Particularly preferred portions of a coding sequence or a complementary sequence are those designed as a probe or primer to detect gene expression. Probes may be labeled by a variety of reporter groups, such as radionuclides and enzymes, and are preferably at least 10 nucleotides in length, more preferably at least 20 nucleotides in length and still more preferably at least 30 nucleotides in length. Primers are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Methods for Diagnosing Cancer

Binding agents (such as OB-cadherin or N-cadherin CAR sequences and antibodies raised against an OB-cadherin or N-cadherin sequence), as well as polynucleotide probes and primers may be used for a variety of diagnostic and assay purposes. In general, such binding agents and polynucleotides may be used to detect a metastatic cancer in a patient, to monitor progression of a cancer or to evaluate the metastatic potential of a cancer. It has been found, within the context of the present invention, that OB-cadherin and/or N-cadherin are expressed by highly invasive cancer cells. Such cells do not generally express E-cadherin at a detectable level. In contrast, highly differentiated, poorly invasive carcinomas express E-cadherin, but do not express OB-cadherin and/or N-cadherin. Accordingly, a metastatic cancer may be detected in a patient based on an elevated level of OB-cadherin or N-cadherin (or RNA encoding OB-cadherin or N-cadherin) present within a biological sample obtained from the patient. Further information regarding metastatic potential of a cancer may be obtained by also evaluating E-cadherin expression within the same or a similar sample.

Biological samples for use within such assays include blood, sera, urine, tumor or normal tissue biopsies, lymph node, peritoneal fluid, cerebrospinal fluid and prostate secretions, as well as other tissues, homogenates, and extracts thereof. For assays employing polynucleotide probes or primers, a biological sample may be a total RNA, mRNA or cDNA preparation from any of the foregoing samples. Such biological samples may be prepared using any standard technique. Samples may be obtained from patients with or without a known cancer (as determined using standard clinical tests).

There are a variety of assay formats known to those of ordinary skill in the art for using a binding agent to detect a target molecule in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

For example, an assay may be performed in a Western blot format, wherein a protein preparation from the biological sample is submitted to gel electrophoresis, transferred to a suitable membrane and allowed to react with an antibody binding agent. The antibody may be labeled, or the presence of the antibody on the membrane may be detected using a suitable detection reagent, as described below. A similar assay may be performed using a peptide binding agent comprising a CAR sequence. Such binding agents are generally labeled, as described below.

In a preferred embodiment, the assay involves the use of binding agent immobilized on a solid support to bind to OB-cadherin or N-cadherin, or a proteolytic fragment thereof, and remove it from the remainder of the sample. The bound cadherin may then be detected using a second binding agent or other detection reagent that contains a reporter group and specifically binds to the binding agent/polypeptide complex. Such detection reagents may comprise, for example, a binding agent that specifically binds to OB-cadherin or N-cadherin. Alternatively, a competitive assay may be utilized, in which OB-cadherin or N-cadherin, or a portion thereof, is labeled with a reporter group and allowed to bind to the immobilized binding agent after incubation of the binding agent with the sample. The extent to which components of the sample inhibit the binding of the labeled OB-cadherin or N-cadherin to the binding agent is indicative of the reactivity of the sample with the immobilized binding agent, and as a result, indicative of the level of OB-cadherin or N-cadherin in the sample.

The solid support may be any material known to those of ordinary skill in the art to which the binding agent may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. A binding agent, such as an antibody or peptide, may be immobilized on the solid support using a variety of techniques known to those in the art, which are amply described in the patent and scientific literature.

In certain embodiments, the assay for detection of OB-cadherin or N-cadherin in a sample is a two-antibody sandwich assay. This assay may be performed by first contacting an antibody that has been immobilized on a solid support, commonly the well of a microtiter plate, with the biological sample, such that OB-cadherin or N-cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme (such as horseradish peroxidase), substrate, cofactor, inhibitor, dye, radionuclide, luminescent group, fluorescent group or biotin) capable of binding to a different site on the cadherin is added. The conjugation of antibody to reporter group may be achieved using standard methods known to those of ordinary skill in the art. The amount of second antibody that remains bound to the solid support is then determined using a method appropriate for the specific reporter group.

More specifically, once an antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptides within the sample are allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of OB-cadherin or N-cadherin within a sample obtained from an individual with a metastatic cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of OB-cadherin or N-cadherin in a sample, using well known techniques.

To determine the presence or absence of a metastatic cancer, the signal detected from the reporter group that remains bound to the solid support is generally compared to a signal that corresponds to a predetermined cut-off value. In one preferred embodiment, the cut-off value for the detection of a metastatic cancer is the average mean signal obtained when the immobilized antibody is incubated with samples from patients without a detectable cancer. In general, a sample generating a signal that is statistically greater (preferably two fold greater) than the predetermined cut-off value is considered positive for a metastatic cancer. The precise cancer may be determined based on location of a tumor and/or using other clinically acceptable diagnostic techniques.

It will be apparent that numerous other assay protocols exist that are suitable for use with the antigens or binding agents of the present invention. For example, flow cytometry techniques may be applied, as described by Seline et al., *J. Invest. Dermatol.* 106:1320–1324, 1996. The above descriptions are intended to be exemplary only.

In another embodiment, binding agents may be used to monitor the progression of a cancer. In this embodiment, assays as described above for the diagnosis of a metastatic cancer may be performed over time, and the change in the level of reactive polypeptide(s) evaluated. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Samples suitable for immunocytochemical staining of OB-cadherin may be prepared by any of a variety of techniques. For example, frozen or paraffin-embedded tissue sections may be prepared as described by Byers et al., *Endocrinology* 134:630–639, 1994 and Cyr et al., *Endocrinology* 130:353–363, 1992, respectively, and placed on glass slides. Alternatively, cells obtained from sources such as peripheral blood or ascites fluid may be fixed onto glass slides as described by Blaschuk and Farookhi, *Dev. Biol.* 136:564–567, 1989. Samples may then be probed using an anti-OB-cadherin antibody or labeled peptide comprising a CAR sequence, using standard techniques.

As noted above, a metastatic cancer may also, or alternatively, be detected based on the level of mRNA encoding OB-cadherin or N-cadherin in a biological sample. For example, at least two oligonucleotide primers may be employed in a polymerase chain reaction (PCR) based assay to amplify a portion of OB-cadherin or N-cadherin cDNA derived from a biological sample, wherein at least one of the oligonucleotide primers is specific for (i.e., hybridizes to) a polynucleotide encoding OB-cadherin or N-cadherin. The amplified cDNA is then separated and detected using techniques well known in the art, such as gel electrophoresis. Similarly, oligonucleotide probes that specifically hybridize to a polynucleotide encoding OB-cadherin or N-cadherin may be used in a hybridization assay to detect the presence of polynucleotide encoding the antigen in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding OB-cadherin or N-cadherin that is at least 10 nucleotides, and preferably at least 20 nucleotides, in length. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule encoding OB-cadherin. Techniques for both PCR based assays and hybridization assays are well known in the art.

One preferred assay employs reverse transcriptase-polymerase chain reaction (RT-PCR), in which PCR is applied in conjunction with reverse transcription. Typically, RNA is extracted from a sample tissue using standard techniques (e.g., guanidine isothiocyanate extraction as described by Chomczynski and Sacchi, *Anal. Biochem* 162:156–159, 1987) and is reverse transcribed to produce cDNA molecules. This cDNA is then used as a template for a subsequent polymerase chain reaction. The cDNA is hybridized to sets of primers, at least one of which is specifically designed against an OB-cadherin or N-cadherin sequence. Examples of OB-cadherin primer sets include, but are not limited to: Forward 5'-ACCAGATGTCTGTATCAGA-3' (SEQ ID NO:315) and Reverse 5'-GTCTCCTGGTCAT CATCTGCA-3' (SEQ ID NO:316; Munro and Blaschuk, *Biol. Reprod.* 55:822–827, 1996); or Forward 5'-GCCAGACACAGTTCTTAAGG-3' (SEQ ID NO:317) and Reverse 5'-ATCAAACCTGAGTATCAGTA-3' (SEQ ID NO:318; Goomer et al., *Calcif. Tissue Int.* 62:532–537, 1998). Once primer and template have annealed, a DNA polymerase is employed to extend from the primer, thus synthesizing a copy of the template. The DNA strands are then denatured and the process is repeated numerous times until sufficient DNA is generated to allow visualization by ethidium bromide staining and agarose gel electrophoresis.

Amplification may be performed on samples obtained from biological samples taken from a test patient and an individual who is not afflicted with a metastatic cancer. The amplification reaction may be performed on several dilutions of cDNA spanning two orders of magnitude. A statistically significant (preferably at least two-fold) increase in expression in several dilutions of the test patient sample as compared to the same dilutions of the non-cancerous sample is typically considered positive for the presence of metastatic cancer. Polynucleotide probes may also be used within in vivo diagnostic assays performed directly on a tumor.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a binding agent as described herein. Such binding agents may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of binding.

Alternatively, a kit may be designed to detect the level of mRNA encoding OB-cadherin or N-cadherin in a biological sample. Such kits generally comprise at least one oligonucleotide probe or primer, as described above, that hybridizes to a polynucleotide encoding OB-cadherin or N-cadherin. Such an oligonucleotide may be used, for example, within a PCR or hybridization assay. Additional components that may be present within such kits include a second oligonucleotide and/or a diagnostic reagent or container to facilitate the detection of a polynucleotide encoding OB-cadherin or N-cadherin.

The following Examples are offered by way of illustration and not by way of limitation.

EXAMPLES

Example 1

Disruption of Human Breast Cancer Cell Adhesion

This Example illustrates the ability of a representative linear peptide comprising an OB-cadherin cell adhesion recognition sequence to disrupt human breast epithelial cell adhesion.

Figure 4A:
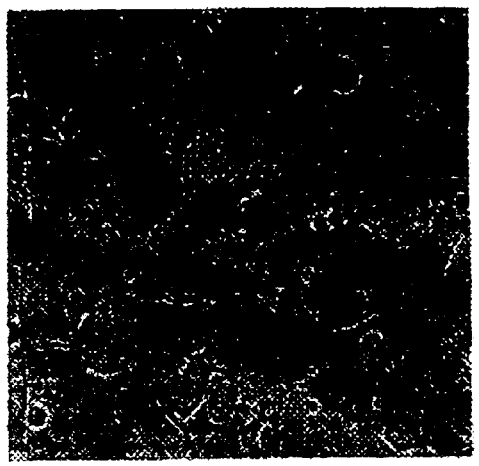
FIGS. 4A–4C are photographs showing cultures of human breast cancer cells in the presence (FIGS. 4B and 4C) and absence (FIG. 4A) of a representative linear OB-cadherin peptide.
Figure 4B:
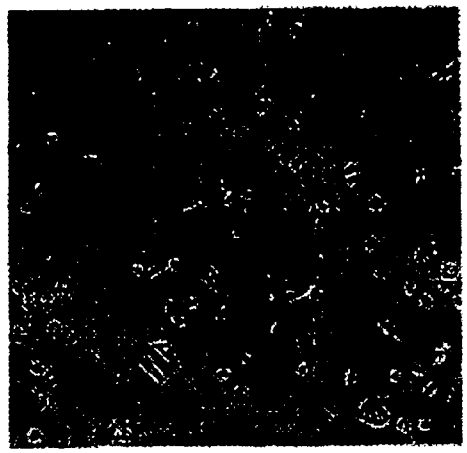
Figure 4C:

MDA-MB-231 human metastatic breast cancer cells (Lombardi Cancer Research Center, Washington, D.C.) were used in these experiments. They express cadherin-11 (also known as OB-cadherin) but not N-cadherin or E-cadherin. The cells were plated (~50,000 cells) on glass coverslips and cultured for 24 hours in DMEM containing 5% serum. Peptides (N-Ac-IFVIDDKSG-NH$_2$ (SEQ ID NO:9) and H-IFVIDDKSG-OH (SEQ ID NO:3)) were dissolved in sterile water (10 mg/ml), and 100 µl of each peptide stock solution was added to 1 ml of DMEM containing 5% serum. Control cells had 100 µl of water added to the medium. Cells were monitored by phase contrast microscopy. After 24 hours cells were fixed in formaldehyde. After 24 hours, neither the peptide H-IFVIDDKSG-OH (SEQ ID NO:3) nor water had an effect on cell morphology (FIG. 4A). The cells treated with either water or H-IFVIDDKSG-OH (SEQ ID NO:3) remained flattened and well-attached to the substratum. In contrast, the cells treated with N-Ac-IFVIDDKSG-NH$_2$ (SEQ ID NO:9) rounded up from each other and were not well-attached to the substratum (FIGS. 4A and 4B; arrows indicate rounded cells). These results demonstrate that the peptide N-Ac-IFVIDDKSG-NH$_2$ (SEQ ID NO:9) interferes with cell adhesion. The amino acid sequence of this peptide is identical to that which is found in the first extracellular domain of OB-cadherin. These results indicate that these metastatic breast cancer cells express OB-cadherin.

Example 2

Detection of OB-cadherin in Metastatic Ovarian Tumor Cells

This Example illustrates the association between OB-cadherin expression and metastasis in ovarian carcinoma cells.

An RT-PCR approach was employed to assay the presence of OB-cadherin mRNA transcripts in two ovarian cancer cell lines: SKOV3 (a metastatic cell line) and OVCAR3 (a noninvasive cell line). The cDNA was synthesized from 1 µg of total RNA by M-MLV-Reverse Transcriptase (Gibco/BRL, Burlington, ON) using a random hexamer as a primer. PCR was performed using the contents of the first-strand reaction and the OB cadherin-specific primers and Taq polymerase (Boehringer Mannheim, Laval, Que., Canada). The OB-cadherin-specific primers used were:

Forward 5'-ACCAGATGTCTGTATCAGA3' (SEQ ID NO:315); and

Reverse 5'-GTCTCCTGGTCATCATCTGCA-3' (SEQ ID NO:316)

(Munro and Blaschuk, *Biol. Reprod.* 55:822–827, 1996). To confirm the quality of the RNA used, PCR was also performed using primers for the housekeeping gene, hypoxanthine phosphoribosyltransferase (HPRT). The HPRT-specific primers used were:

Forward 5'-CCTGCTGGATTACATTAAAGCACTG-3' (SEQ ID NO:319); and

Reverse 5'-GTCAAGGGCATATCCAACAACAAAC-3' (SEQ ID NO:320)

(Melton et al., *Proc. Natl. Acad. Sci. USA* 81:2147–2151, 1984). The cycling program was as follows: denaturation at 95° C. for 30 sec.; annealing at 58–60° C. for 45 sec.; polymerization at 72° C. for 1 min.; repeat for 30 cycles. All PCR reactions were performed in parallel with reactions containing no cDNA as a control for contamination of PCR reagents. Products were identified by agarose gel electrophoresis stained with ethidium bromide (Sambrook et al., *Molecular Cloning: A Laboratory Manual,* Cold Spring Harbor Laboratories, Cold Spring Harbor, N.Y., 1989).

Figures 5, 6:
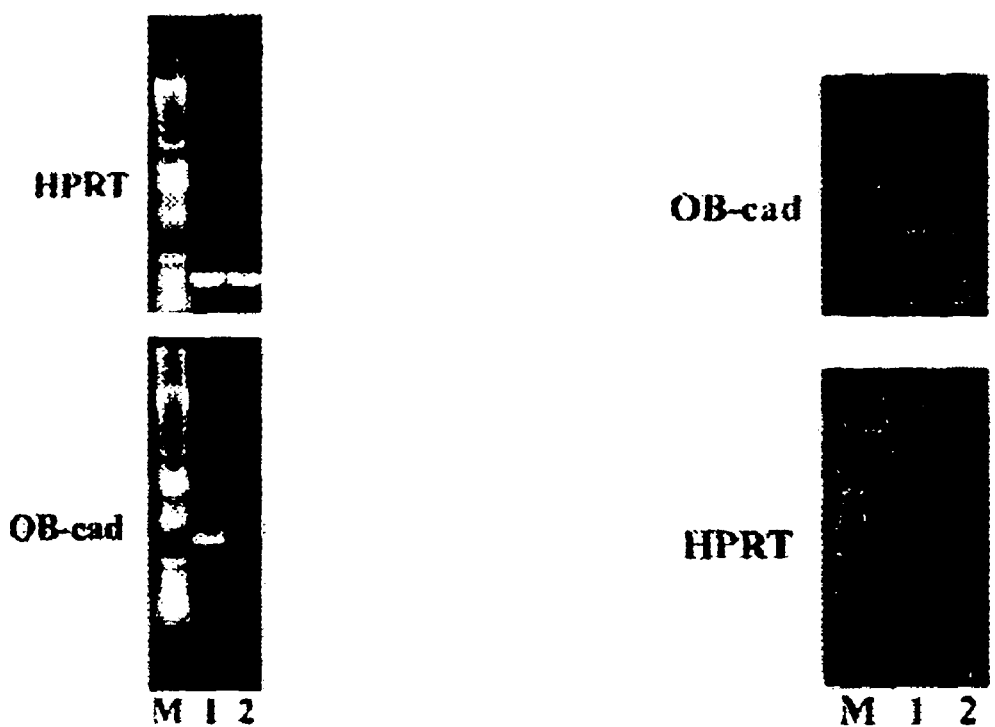
FIG. 5 is a photograph illustrating the results of PCR analysis to detect the presence of OB-cadherin in metastatic human ovarian cancer cells, but not in well-differentiated human ovarian cancer cells. RT-PCR products from two cell lines are shown: SKOV3 in lane 1 and OVCAR3 in lane 2. The primers used were specific for OB-cadherin (OB-cad) and hypoxanthine phosphoribosyltransferase (HPRT) as indicated, with an expected PCR product of 745 bp and 352 bp, respectively. Products were stained with ethidium bromide and resolved by agarose gel electrophoresis. Lane M represents a 1 kb ladder (Gibco/BRL).
FIG. 6 is a photograph illustrating the results of PCR analysis detecting the presence of OB-cadherin in leukemic cells. RT-PCR products were generated from lymphocytes of a human B-CLL patient (lane 1) and mouse liver (lane 2). The primers used were specific for OB-cadherin (OB-cad, top panel) and hypoxanthine phosphoribosyltransferase (HPRT, bottom panel), with an expected PCR product of 745 bp and 352 bp, respectively. Products were stained with ethidium bromide and resolved by agarose gel electrophoresis. Lane M represents a 1 kb ladder (Gibco/BRL).

The results are presented in FIG. 5, which shows RT-PCR products from SKOV3 (lane 1) and OVCAR3 (lane 2). The primers used are specific for OB-cadherin (OB-cad) and hypoxanthine phosphoribosyltransferase (HPRT) as indicated, with an expected PCR product of 745 bp and 352 bp, respectively. Products were stained with ethidium bromide and resolved by agarose gel electrophoresis, and were all of the expected size. The results indicate that OB-cadherin is expressed by metastatic ovarian cancer cells, and is not expressed by non-invasive ovarian cancer cells.

Example 3

Detection of OB-cadherin in Leukemic Cells

This Example illustrates the expression of OB-cadherin in lymphocytes of leukemia patients.

The RT-PCR approach described in Example 2 was employed to assay the presence of OB-cadherin mRNA transcripts in lymphocytes extracted from patients with B-cell chronic lymphocytic leukemia (B-CLL). RT-PCR products (shown in FIG. 6) were generated from lymphocytes of a human B-CLL patient (lane 1) and mouse liver (lane 2). The primers used were specific for OB-cadherin (OB-cad, top panel) and hypoxanthine phosphoribosyltransferase (HPRT, bottom panel), with an expected PCR product of 745 bp and 352 bp, respectively. Products were stained with ethidium bromide and resolved by agarose gel electrophoresis, and were all of the expected size. The results indicate that lymphocytes of a leukemia patient express OB-cadherin.

Example 4

Expression of N-cadherin in Metastatic Carcinoma Cells

This Example illustrates the correlation between N-cadherin and metastatic potential in ovarian carcinoma cell lines.

E-cadherin and N-cadherin expression was evaluated in a series of ovarian carcinoma cell lines, using the RT-PCR approach described above. The E-cadherin specific primer used were:

Forward 5'-CCTTCCCCCAACACGTCCCCCC-3' (SEQ ID NO:321); and

Reverse 5'-TCTCCACCTCCTTCTTCATC-3' (SEQ ID NO:322)

(Munro and Blaschuk, *Biol. Reprod.* 55:822–827, 1996). The N-cadherin specific primers used were:

Forward 5'-CAAGAGCTTGTCACAATCAGG-3' (SEQ ID NO:323); and

Reverse 5'-CATTTGGATCATCCGCATC-3' (SEQ ID NO:324)

(Munro and Blaschuk, *Biol. Reprod.* 55:822–827, 1996).

Cell lines examined included OVCAR-3 (Hamilton et al., *Cancer Research* 43:5379–89,1983); SW626 (Ripamonti et al., *Cancer Immunology, Immunotherapy* 24:13–18, 1987); CaOV3, SKOV3 and HEY (Buick et al., *Cancer Research* 45:3668–76, 1985). These cells (except HEY) are also available from American Type Culture Collection (Manassas, Va.).

The results of these analyses are presented in Table I, below, in which detectable PCR product is indicated as a "+" and no detectable PCR product is indicated by a "−".

TABLE I

N- and E-Cadherin Expression in Ovarian Carcinoma Cell Lines

| Cell Line | Phenotype | Differentiation Stage and Metastatic Potential | Cadherin E | Cadherin N |
|---|---|---|---|---|
| Normal | Epithelial | None | + | − |
| OVCAR-3 | Adenocarcinoma | Differentiated; low metastatic | + | − |
| SW626 | Adenocarcinoma | Differentiated; low metastatic | + | − |
| CaOV3 | Adenocarcinoma | ? | + | + |
| SKOV3 | Adenocarcinoma | Poor differentiation; high metastatic | − | + |
| HEY | Adenocarcinoma | Poor differentiation; high metastatic | − | + |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining the presence of invasive ovarian or breast cancer cells in a biological sample of a cancer patient, comprising the steps of:
   (a) contacting a biological sample obtained from the cancer patient with a binding agent that specifically binds to an OB-cadherin that comprises SEQ ID NO:4 or SEQ ID NO:5 and modulates cell adhesion of OB-cadherin-expressing cells; and
   (b) detecting in the sample an amount of polypeptide that binds to the binding agent, relative to a predetermined cut-off value, and therefrom determining the presence of invasive cancer cells in the biological sample
   wherein the binding agent is selected from the group consisting of a CAR sequence of OB-cadherin, a monoclonal antibody or a polyclonal antibody.

2. A method according to claim 1, wherein the binding agent specifically binds to an extracellular domain of a human OB-cadherin.

3. A method according to claim 1, wherein the biological sample is selected from the group consisting of blood, serum, urine, tumor biopsies, peritoneal fluid, cerebrospinal fluid, and fractions of the foregoing samples.

4. A method for monitoring the progression of invasive ovarian or breast cancer in a patient, comprising the steps of:
   (a) contacting a biological sample obtained from the patient at a first point in time with a binding agent that specifically binds to an OB-cadherin that comprises SEQ ID NO:4 or SEQ ID NO:5 and modulates cell adhesion of OB-cadherin-expressing cells;
   (b) detecting in the sample an amount of a polypeptide that binds to the binding agent;
   (c) repeating steps (a) and (b) using a biological sample obtained from the patient at a subsequent point in time; and
   (d) comparing the amount of polypeptide detected in step (c) to the amount detected in step (b) and therefrom monitoring the progression of the cancer in the patient, wherein the cancer is progressing if the amount of the polypeptide increases over time, whereas the cancer is not progressing if the amount of the polypeptide remains constant or decreases with time
   wherein the binding agent is selected from the group consisting of a CAR sequence of OB-cadherin, a monoclonal antibody or a polyclonal antibody.

5. A method according to claim 4, wherein the binding agent specifically binds to an extracellular domain of a human OB-cadherin.

6. A method according to claim 4, wherein the biological sample is selected from the group consisting of blood, serum, urine, tumor biopsies, peritoneal fluid, and fractions of the foregoing samples.

* * * * *